United States Patent
Kornilovich et al.

(10) Patent No.: US 7,829,352 B2
(45) Date of Patent: *Nov. 9, 2010

(54) FABRICATION OF NANO-OBJECT ARRAY

(75) Inventors: Pavel Kornilovich, Corvallis, OR (US);
Peter Mardilovich, Corvallis, OR (US);
James Stasiak, Lebanon, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 885 days.

This patent is subject to a terminal disclaimer.

(21) Appl. No.: 11/457,776

(22) Filed: Jul. 14, 2006

(65) Prior Publication Data
US 2007/0020773 A1 Jan. 25, 2007

Related U.S. Application Data

(60) Division of application No. 10/744,516, filed on Dec. 23, 2003, now Pat. No. 7,132,298, which is a continuation-in-part of application No. 10/683,527, filed on Oct. 7, 2003, now Pat. No. 7,223,611.

(51) Int. Cl.
*H01L 21/00* (2006.01)
(52) U.S. Cl. .................. 438/2; 438/3; 977/760; 977/761; 977/762; 977/932; 257/E29.072; 257/E29.298; 257/E21.663
(58) Field of Classification Search .............. 438/2, 438/3; 977/760–762, 932; 257/E29.072, 257/E29.298, E21.663
See application file for complete search history.

(56) References Cited

U.S. PATENT DOCUMENTS

| 7,132,298 B2 * | 11/2006 | Kornilovich et al. .......... 438/3 |
| 7,220,609 B2 * | 5/2007 | Zacharias ................... 438/29 |
| 7,223,611 B2 * | 5/2007 | Kornilovich et al. .......... 438/3 |
| 2003/0135971 A1 * | 7/2003 | Liberman et al. ......... 29/419.1 |
| 2004/0183070 A1 * | 9/2004 | Afzali-Ardakani et al. .... 257/40 |

FOREIGN PATENT DOCUMENTS

| JP | P1992-356963 A | 12/1992 |
| JP | P1995-130956 A | 5/1995 |
| JP | P1998-15857 A | 1/1998 |
| WO | WO03/075372 A2 | 9/2003 |

OTHER PUBLICATIONS

English Translation of Japanese Office Action dated Feb. 26, 2008, 2 pages.
English Abstract of P1992-356963A, 1 page.
English Abstract of P1995-130956A, 1 page.
English Abstract of P1998-15857A, 1 page.

* cited by examiner

*Primary Examiner*—Michelle Estrada

(57) ABSTRACT

This disclosure relates to a system and method for creating nano-object arrays. A nano-object array can be created by exposing troughs in a corrugated surface to nano-objects and depositing the nano-objects within or orienting the nano-objects with the troughs.

34 Claims, 28 Drawing Sheets

FABRICATION OF NANO-OBJECT ARRAY

CROSS REFERENCE TO RELATED PATENT APPLICATION

This application is a divisional application and claims the benefit and priority of U.S. patent application Ser. No. 10/744,516 filed Dec. 23, 2003 now U.S. Pat. No. 7,132,298 which is a continuation-in-part of a co-pending U.S. patent application having Ser. No. 10/683,527, with a filing date of Oct. 7, 2003 now U.S. Pat. No. 7,223,611, issued May 29, 2007.

TECHNICAL FIELD

This invention relates to a system and method for fabricating nano-object arrays.

BACKGROUND

Prior art thin-wire arrays are used in a large number of devices, and have been found particularly suited for use in small or densely structured computer devices, such as sensors, memory devices, and logic chips.

To address this need for thin-wire arrays, thin-wire arrays have been created using photolithography. As computer devices get smaller and smaller, however, the wires of these arrays need to be thinner and more closely spaced. Photolithography has so far not proven to be an adequate method to create very thin and closely spaced arrays of wires.

To address this need for thinner arrays of wires, two ways of creating them have been used. One of these prior-art ways uses an etched superlattice as a mold for imprint lithography. The other uses an etched superlattice and physical vapor deposition to fabricate nanowire arrays.

Prior-art etched-superlattice imprint lithography is described in U.S. Pat. No. 6,407,443. This example of imprint lithography is typically associated inconveniently with subsequent lift-off processing and may ultimately have limited process capability. It also uses a nano-imprinting step, which has so far not been consistently and successfully used in a production atmosphere.

Prior-art physical vapor deposition uses an atomic beam to directly deposit material on a surface of an etched superlattice. This deposited material is then physically transferred to a substrate. This method, however, may produce oddly shaped wires, which can create various structural and usage difficulties. Prior-art physical vapor deposition also can require processing in an Ultra-High Vacuum ("UHV"), which can be costly to use and would restrict the usage of materials that are incompatible with UHV processing.

There is, therefore, a need for a technique for manufacturing arrays of thinner wires that is reliable, less expensive, more reproducible, and more production-friendly than permitted by present-day techniques.

BRIEF DESCRIPTION OF THE DRAWINGS

The same numbers are used throughout the disclosure and figures to reference like components and features.

DETAILED DESCRIPTION

The following disclosure describes various embodiments of a system and method for fabricating nanowire and nano-object arrays. The described system and method can be used to fabricate arrays of wires or objects with a thickness and spacing in a nano, micro, and meso scale and in combinations of these scales. The described system and method can be used to fabricate arrays of wires or objects directly on the side of a superlattice. Such arrays can be used to fabricate secondary arrays of wires on a different substrate surface. Such secondary arrays can be used to fabricate further arrays of different wires or objects on the same substrate surface. This nesting of capabilities for the processing of arrays provides great flexibility in material selection, process design, and the engineering of structures and devices.

The disclosed system and method is capable of creating an array of closely spaced, very thin wires or objects. This type of array is capable of being used in current and future devices, allowing these devices to function better, more quickly, and be built on a smaller scale.

The disclosed system and method offer substantial benefits over many prior-art solutions. These benefits can include precise control of the dimensions of an array, such as a length, thickness, and spacing of wires or objects, as well as a number of wires or objects. The disclosed system can also provide smoother, more usable cross-sections of the wires than some prior-art solutions. Further, the cost of producing nanowire and nano-object arrays can be reduced with this system and method, including by using a superlattice multiple times and not needing to use nano-imprinting, lift-off processes, or UHV, each of which can be costly. Also, nanowire and nano-object arrays having wires or objects made of many different types of materials can also be created using the described system and method—a potentially substantial benefit.

An Exemplary Superlattice

FIGS. 1 through 4 set forth a superlattice usable in various processes discussed below for creating a nanowire or nano-object array. This superlattice is one example of a structure usable in the below-discussed processes. Other superlattices, surfaces, and structures can be used; this exemplary superlattice is not intended to be limiting on the scope of the below processes, but instead is intended to aid the reader in understanding the below-described processes.

Figure 1:
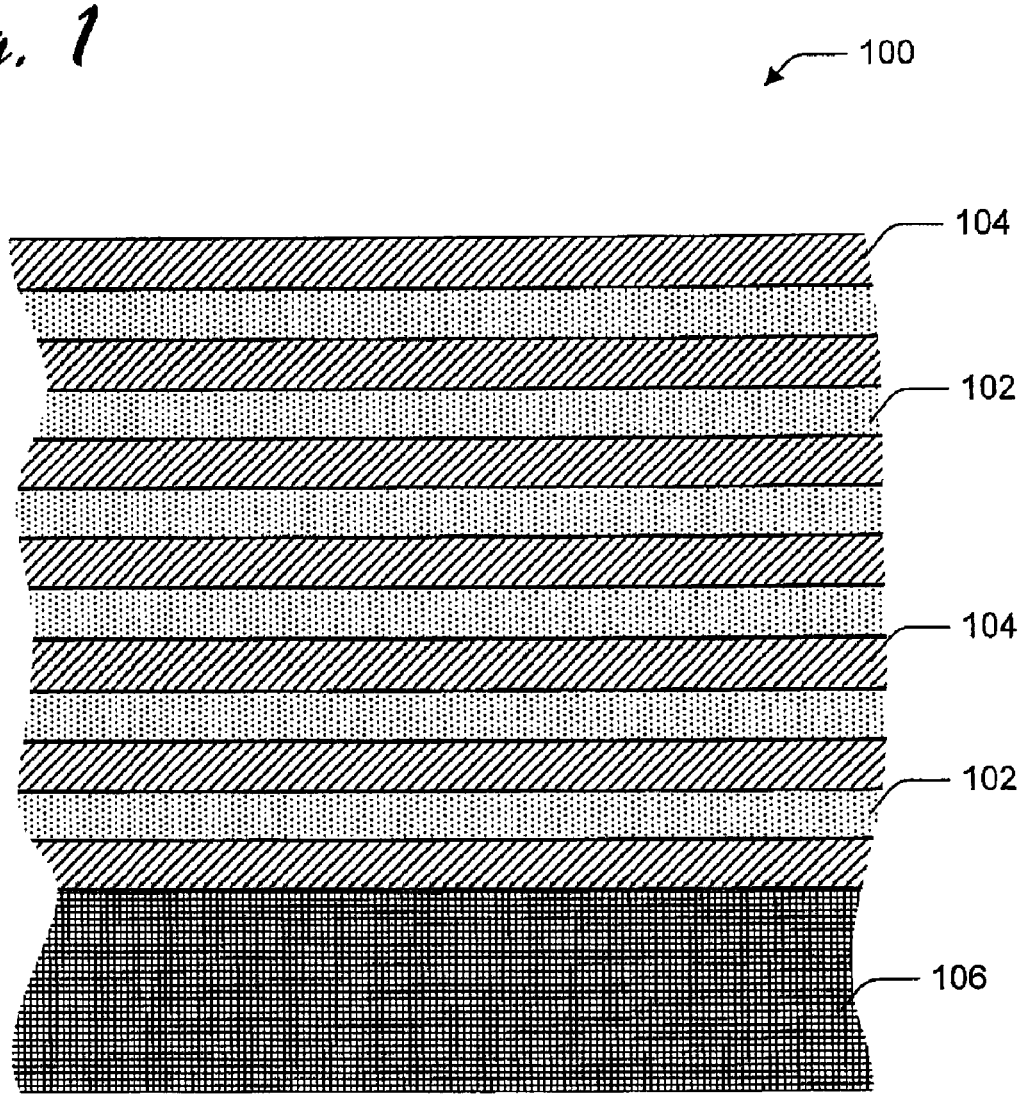
FIG. 1 illustrates a side, cross-sectional view of an exemplary superlattice.

FIG. 1 sets forth an exemplary superlattice 100, here shown at a side, cross-sectional view. The superlattice 100 includes at least two or more different layered materials, here first material layers 102 and second material layers 104. Either of these material layers can be layered on a substrate 106, or otherwise. Construction of the superlattice 100 shown in FIG. 1 can be performed in various ways, such as with chemical vapor deposition, sputtering and other methods of physical vapor deposition, atomic layer deposition, electroplating, and the like.

The layered materials alternate, such as shown in FIG. 1. The thickness of each of the layers 102 and 104 affects the process of creating a spacing (or "pitch") between wires or objects and a thickness of the wires (and, in some cases the objects) themselves, as will be set forth in greater detail below. Thus, the thickness and spacing of the layers 102 and 104 affect the properties of an array of wires or objects fabricated using the superlattice 100.

Both of the first material layers 102 and the second material layers 104 can be of various thicknesses, including from nanometer in scale to micrometer and thicker in scale. The layers 102 and 104, for instance, can be created with a thickness of less than 10 nanometers (even as low as 0.7 nanometers), 10-15 nanometers, 15-20 nanometers, and 20 to 50 nanometers or more, or combinations thereof. The smallest layer thicknesses are used to produce wire or object arrays of the highest density and wires or objects that exhibit extreme size-dependent properties such as quantum effects. The larger layer thicknesses provide for classical non-quantum properties, easier manufacturability, greater electrical conductance, more surface area, and less dense arrays.

The first material layers 102 can be made of various types of materials, including conductive materials and non-conductive materials. Of conductive materials, the first material layers 102 can include one or more metals such as platinum, beryllium, aluminum, palladium, tantalum, nickel, gold; metallic alloys; a ceramic such as indium tin oxide, vanadium oxide, or yttrium barium copper oxide; an electrically semi-conductive material such as silicon, diamond, germanium, gallium arsenide, cadmium telluride, zinc oxide, silicon carbide, tin oxide, indium tin oxide; and/or other elemental, binary, and multi-component materials, for instance. Of the non-conductive materials, the first material layers 102 can include aluminum oxide, various other oxides, and other insulating materials that can be deposited in thin layers. The choice of material combination will be application-specific, and the process can be made to work with most any solid material that can be deposited as thin layers, including "soft" materials like polymers.

Likewise, the second material layers 104 can be made of various types of materials, including conductive materials and non-conductive materials, such as those described for the first material layers 102, above. Of the non-conductive materials, the second material layers 104 can include aluminum oxide, various other oxides, and other insulating materials that can be deposited in thin layers. Also the first material layers 102 and the second material layers 104 can be single-crystalline and/or in epitaxial relationship. Epitaxial refers to the perfect or near-perfect lattice registry of one material to another material upon which it is deposited.

Both the first material layers 102 and the second material layers 104 can be conductive, or one of them can be conductive and the other insulative. In cases where both of the layers 102 and 104 are conductive, a surface that exposes the layers can be treated such that one exposed surface of either the first material layers 102 or the second material layers 104 is non-conductive, etched, or removed. These processes and an example of the surface will be described in greater detail below.

Both of the first material layers 102 and the second material layers 104 can include more than one material. The first material layers 102 can, for instance, include layers some of which include gold, some of which include tantalum, some of which include nickel, and the like.

The superlattice 100 and the first material layers 102 and the second material layers 104 have a thickness, a length, and a depth. The first and second material layers 102 and 104 can have a length that is nanometer in scale up to centimeter in scale. Depending on the eventual application for the array, the wires or objects may need to be very short (nanometer scale in length) or quite long (centimeter scale in length). As will be discussed in greater detail below, the eventual length of the wires or objects in the array can be related to the length of the superlattice 100 and its first material layers 102 and/or its second material layers 104.

Figure 2:
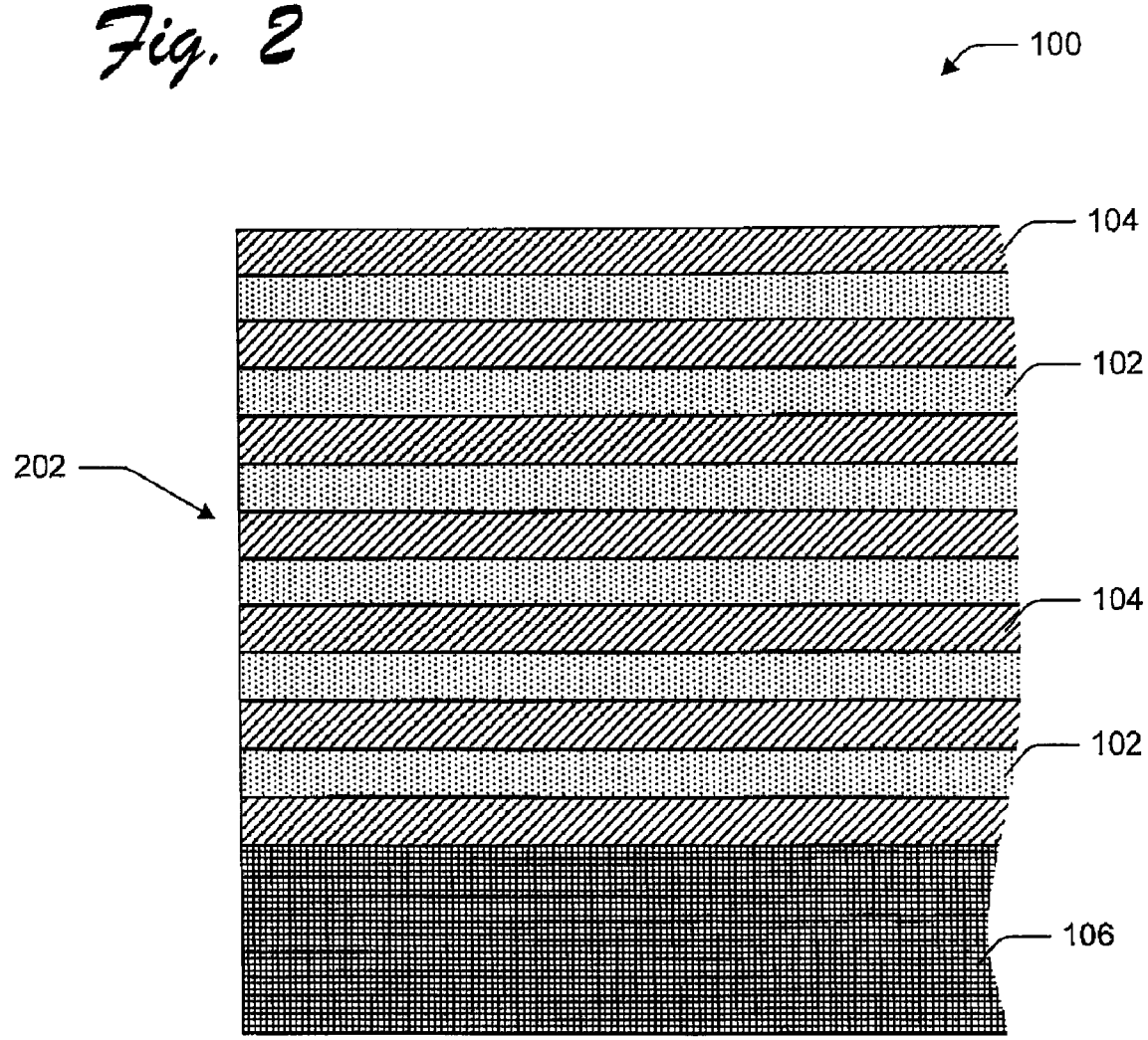
FIG. 2 illustrates a side, cross-sectional view of an exemplary superlattice having a working surface.

FIG. 2 sets forth an example of the superlattice 100, here shown at a side, cross-sectional view, and having a working surface 202. Here the superlattice 100 is altered to create the working surface 202. This working surface 202 is substantially level (planar) at some portion, this level portion being usable to aid in creating the wires of the nanowire array (discussed below). The working surface 202 can be created in various ways, including by cutting and polishing the superlattice 100.

The working surface 202 can be substantially parallel to a thickness of the first material layers 102 and the second material layers 104 or otherwise. If the working surface 202 is not substantially parallel to the material layers' 102 and 104 thickness, greater area of the material layers 102 and 104 will be exposed. With a greater area of the material layers 102 and 104 exposed, wires created with the working surface 202 can be created thicker than if the working surface 202 is substantially parallel to the thickness of the first and second material layers 102 and 104. If the working surface 202 is substantially parallel with the thickness of the material layers, the working surface 202 is usable to aid in creating wires, orienting nano-objects, and creating spaces between wires or objects in the array that are about the same as the thickness of the first and second material layers 102 and 104.

Figure 3:
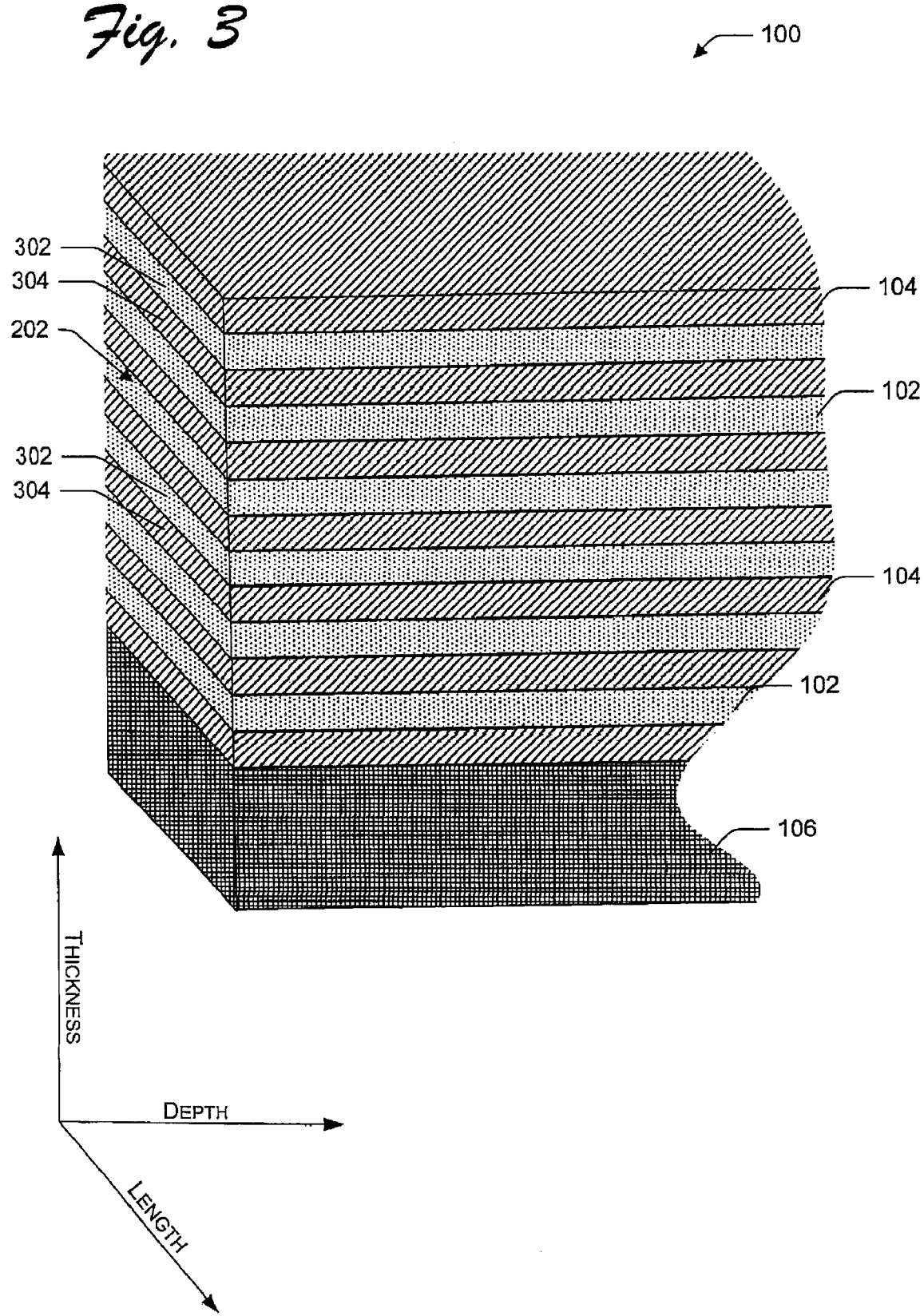
FIG. 3 illustrates a three-dimensional view of an exemplary superlattice having a working surface and thickness, depth, and length dimensions.

FIG. 3 sets forth a three-dimensional view of an example of the superlattice 100 with the working surface 202. Here the working surface 202 is shown exposing multiple areas, or edges, of the first and second material layers 102 and 104. These edges are referenced as first material edges 302 and second material edges 304. These exposed edges 302 and 304 can be used to aid in creating wires or collecting and orienting nano-objects of the array, as will be discussed in greater detail below.

Figure 4:
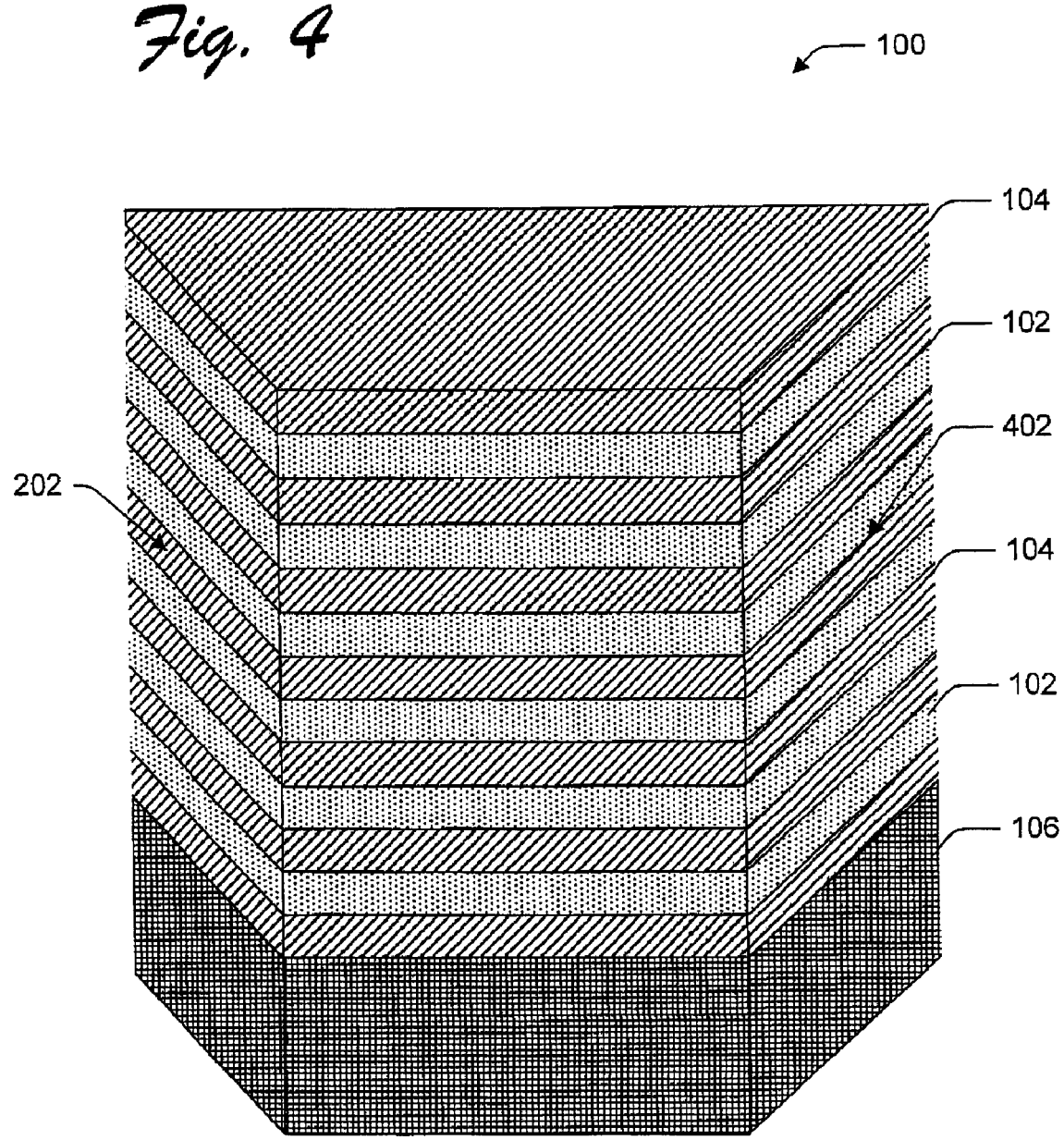
FIG. 4 illustrates a three-dimensional view of an exemplary superlattice having a working surface and an electrical connection surface.

FIG. 4 sets forth a three-dimensional view of an example of the superlattice 100 with an example of the working surface 202 and an exemplary electrical connection surface 402. Here the superlattice 100 is altered to create the electrical connection surface 402. The electrical connection surface 402 does not need to be substantially level at some portion, though connection to an electrical power sink can be easier if it is substantially level or planar. The electrical connection surface 402 can be created in various ways, including by cutting and polishing the superlattice 100.

Exemplary Platform for Creating Nanowire and Nano-Object Arrays

Figure 5:
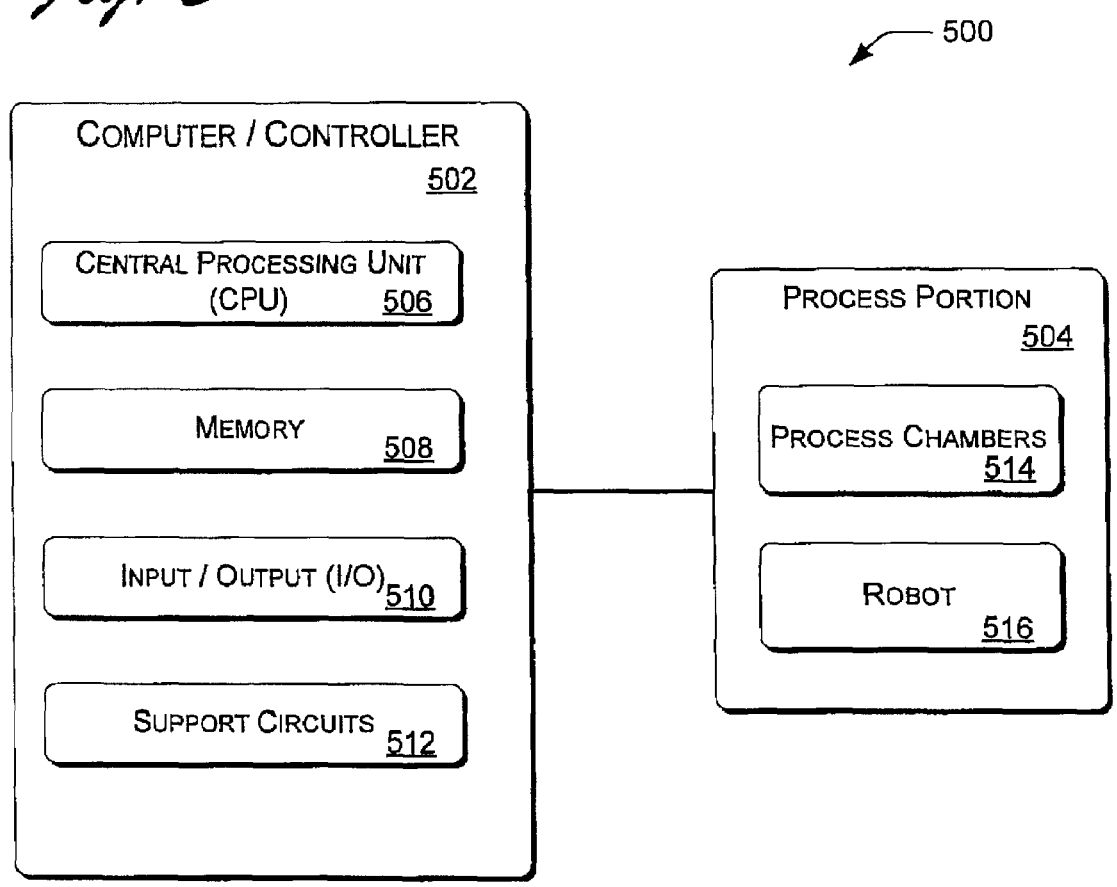
FIG. 5 shows a block diagram of an exemplary system that is capable of implementing methods for creating nanowire and nano-object arrays.

FIG. 5 illustrates one embodiment of a platform 500 usable to perform methods set forth below for creating nanowire and nano-object arrays. The platform 500 includes a computer/controller 502 and a process portion 504.

The computer/controller 502 includes a central processing unit (CPU) 506, a memory 508, input/output (I/O) circuits 510, and support circuits 512. The CPU 506 is a general purpose computer which, when programmed by executing software contained in memory 508 (not shown), becomes a directed-purpose computer for controlling the hardware components of the processing portion 504. The memory 508 may include read-only memory, random-access memory, removable storage, a hard disk drive, or any form of digital memory device. The I/O circuits 510 comprise well-known displays for the output of information and a keyboard, a mouse, a track ball, or an input of information that can allow for programming of the computer/controller 502 to determine the processes performed by the process portion 504 (including the associated robot action included in the process portion 504). The support circuits 512 may be known in the art and include circuits such as cache, clocks, power supplies, and the like.

The memory 508 contains control software that, when executed by the CPU 506, enables the computer/controller 502 to digitally control the various components of the process portion 504. A detailed description of the process that is implemented by the control software is described with respect to FIGS. 6, 16, and 20.

In another embodiment, the computer/controller 502 can be analog. For instance, application-specific integrated circuits capable of controlling processes such as those that occur within the process portion 504 can be used.

The process portion 504 may include a variety of process chambers 514 between which the substrate 106 and/or the superlattice 100 is translated, often using a robot mechanism 516. The particulars of the processing varies with different methods described below.

Exemplary Methods for Creating Nanowire Arrays

Figure 6:
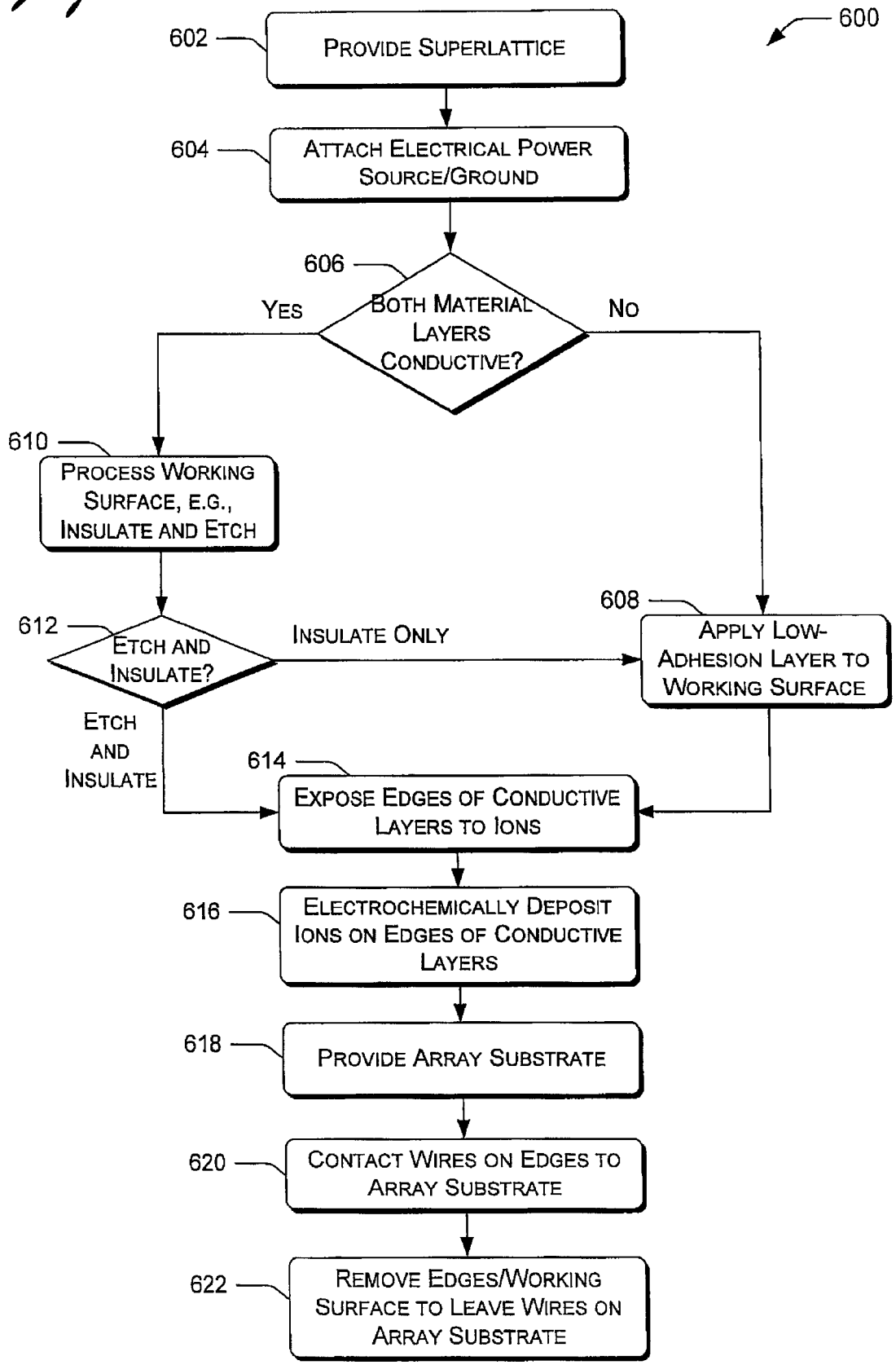
FIG. 6 is a flow diagram of an exemplary method for creating a nanowire array using electrochemistry and physical transfer.

FIG. 6 shows an exemplary flow diagram of a process 600 for electrochemically creating a nanowire array. This and the following processes are illustrated as a series of blocks representing operations or acts performed by the platform 500. These processes may be implemented, however, in any suitable robotics, persons, hardware, software, firmware, or combination thereof. In the case of software and firmware, they represent sets of operations implemented as computer-executable instructions stored in memory and executable by one or more processors.

At block 602 the superlattice 100 is provided.

At block 604, the superlattice 100 is attached or otherwise put in electrical communication with an electrical power source or an electrical ground (sink).

Figure 7:
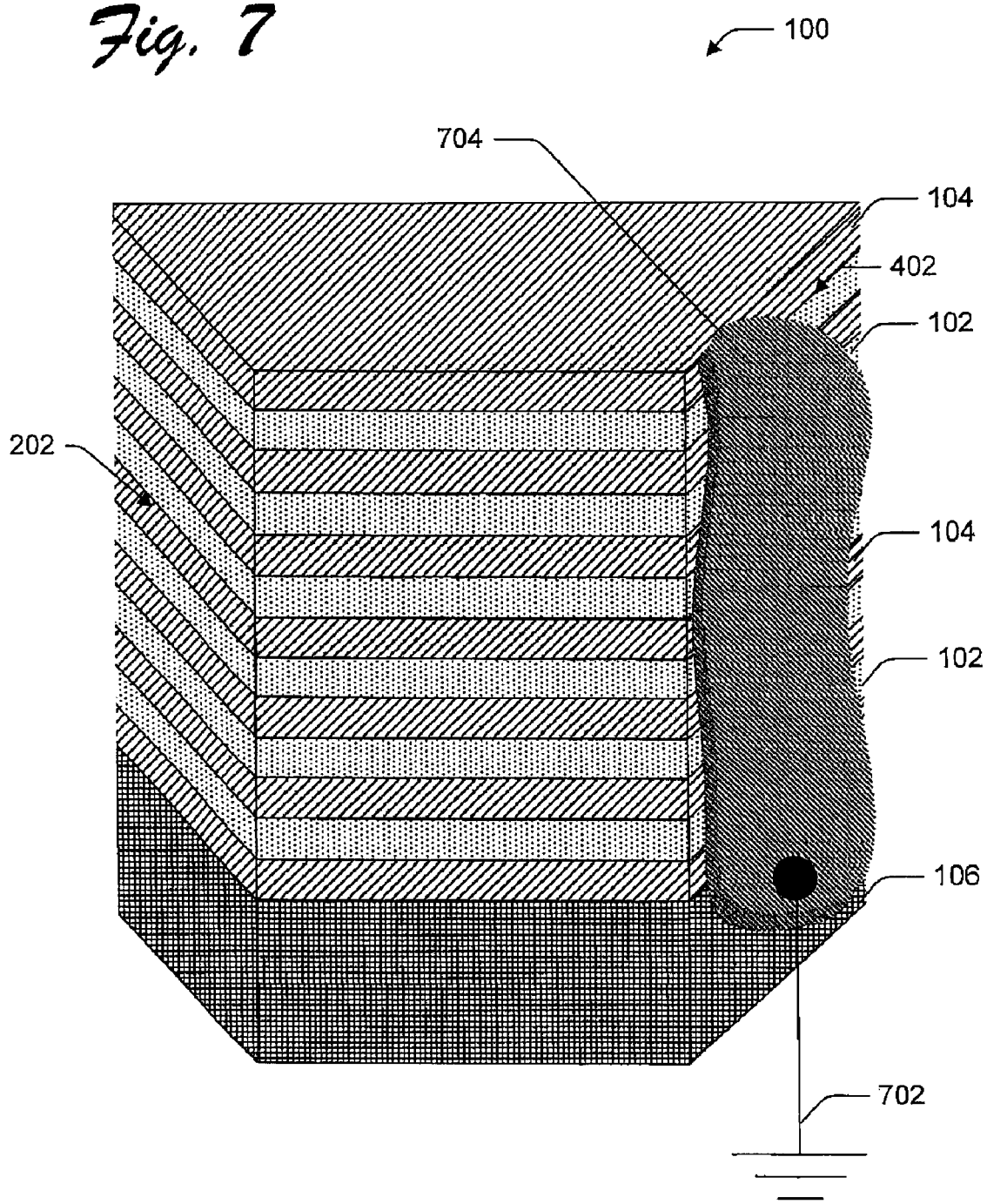
FIG. 7 illustrates a three-dimensional view of an exemplary superlattice having a working surface and an electrical connection surface in electrical communication with an electrical power sink.

FIG. 7 sets forth a three-dimensional view of an example of the superlattice 100 with examples of the working surface 202 and the electrical connection surface 402, the electrical connection surface 402 being in electrical communication with an electrical power sink 702.

With the electrical connection surface 402 being put in communication with the electrical power sink 702, there can be a voltage difference between the first and second material layers 102 and 104 at the working surface 202 and ions, conductive substrates, and other devices (not yet shown). This voltage difference can be used to transfer ions to or from the working surface 202 to create wires for a nanowire array or attract objects to build a nano-object array. How this voltage difference can be used to facilitate creation of an array will be discussed in greater detail below.

If material(s) of the first material layers 102 or the second material layers 104 are non-conductors, and thus non-conductive from the working surface 202 to the electrical connection surface 402, the electrical connection surface 402 is constructed such that each layer of the other material layer (which is/are conductors) connects with the electrical power sink 702. In this case, the electrical connection surface 402 is prepared such that each conductive layer of the conductive material layer is in electrical communication with the electrical power sink 702. This can be accomplished by cutting and polishing the electrical connection surface 402 and then placing a conductive connection material 704 in contact with each of the conductive layers at the electrical connection surface 402. It can be accomplished in other ways as well, with the goal being that each layer of the conductive material layer be in communication with an electrical power sink if that layer is intended to be used to aid in creating a wire or orienting a nano-object for the array.

If the materials of both the first and second material layers 102 and 104 are conductors, the electrical connection surface 402 can be prepared without the conductive connection material 704. In this case, the electrical power sink 702 can be connected directly to one or more of the layers, or to a smaller amount of material that is connected directly to one or more of the layers.

At block 606, if the materials in both of the first material layers 102 and the second material layers 104 are conductive, the platform 500 proceeds along the "No" path to block 608. If yes, the platform 500 proceeds along the "Yes" path to block 610.

At block 608, the platform 500 applies a low-adhesion layer to the working surface 202. This low-adhesion layer can be nano-scale in depth, or even less than one nanometer in depth. The low-adhesion layer should be thin enough and have properties such that it does not substantially interfere with a conductive property of the first or second material edges 302 or 304 that is conductive.

Figure 8:
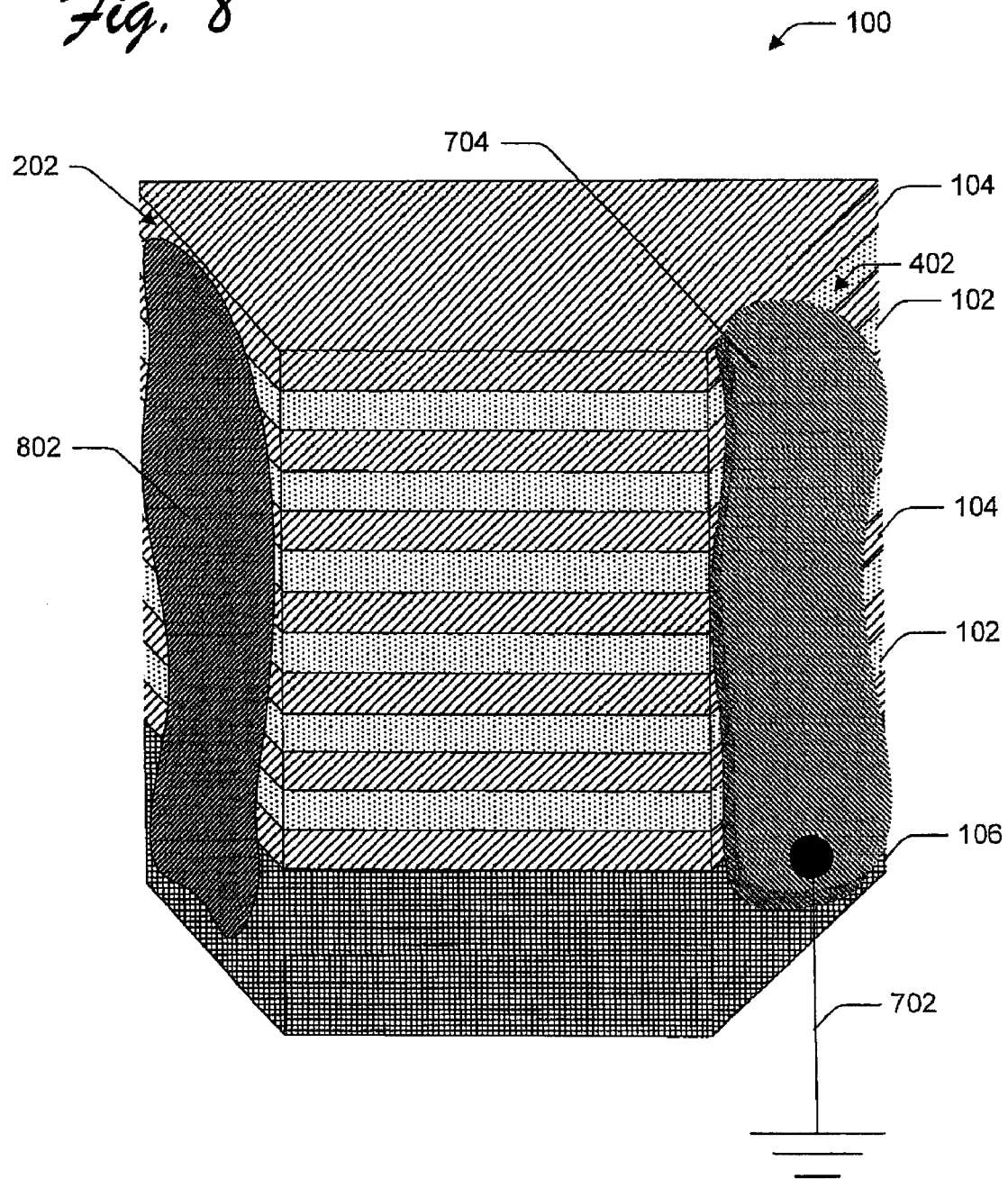
FIG. 8 illustrates a three-dimensional view of an exemplary superlattice having a working surface having a low-adhesion layer and an electrical connection surface in electrical communication with an electrical power sink.

FIG. 8 sets forth a three-dimensional view of an example of the superlattice 100 with examples of the working surface 202, the electrical connection surface 402, the electrical power sink 702, and an exemplary low-adhesion layer 802. In some implementations of the system and method, the low-adhesion layer 802 is added to the superlattice's 100 working surface 202. This low-adhesion layer 802 acts to allow wires that are created on the working surface 202 to more easily be removed from the working surface 202. The removal of these wires can be made easier by addition of the low-adhesion layer 802 by lowering adhesion between these wires (not shown in FIG. 8) and the working surface 202.

The low-adhesion layer 802 can be of varying adhesive force, from very low to moderately high adhesion. Some of the adhesion layer 802 can come off with the wires when the wires are removed from the working surface 202, or substantially all of it can remain with the working surface 202. The low adhesion layer 802 helps to reduce incidence of wires sticking to the working surface 202, or being broken or otherwise damaged on removal by too high an adhesion force between the wires and the working surface 202. It can have varying strength of adhesion, such as an adhesion strength to eventual wires created on the working surface 202 that is of a strength lower than the strength of an eventual substrate to which the wires are transferred. To reduce the amount of the low-adhesion layer sticking to the wires, the low-adhesion layer can adhere to the working surface 202 with greater force than to the wires.

In other implementations, the low-adhesion layer 802 is not used. These implementations will be discussed in greater detail below.

At block 610, the platform 500 processes the working surface 202 of the superlattice 100. This process can include causing exposed edges of the first material layers 102 or the second material layers 104 to be non-conductive. It can also include preferentially exposing edges of one of the first or second material layers 102 and 104.

In the case of causing certain exposed edges to be non-conductive, the platform 500 can insulate certain layers of the first and/or second material layers 102 and 104. The platform can, for instance, oxidize or nitridize exposed edges of certain layers to insulate them.

In one implementation, for instance, the edges of the second material layers 104 are insulated at block 610 while the first material layers 102 are not. This can be performed by oxidizing the second material edges 304 (see FIG. 3). In one implementation, the platform 500 exposes the working surface 202, and thus the first material edges 302 and the second material edges 304, to an oxygen atmosphere. In this implementation, the first material edges 302 do not oxidize as quickly as the second material layers 304. Because of this, the second material layers 304 can be oxidized sufficiently to become non-conductive prior to the first material edges 302 becoming non-conductive.

In another implementation, edges of one of the first and second material layers 102 and 104 are insulated through nitridation. In this implementation, the platform 500 exposes the working surface 202 (along with the first and second edges 302 and 304) to a nitrogen atmosphere under proper conditions of pressure, temperature, plasma, and/or catalyst, etc. Here, one of the first and second material edges 302 and 304 are nitrided sufficiently to be non-conductive at the working surface 202. The material edge that is to remain conductive has a nitridation rate that is lower than the material edge to be made non-conductive.

Figure 9:
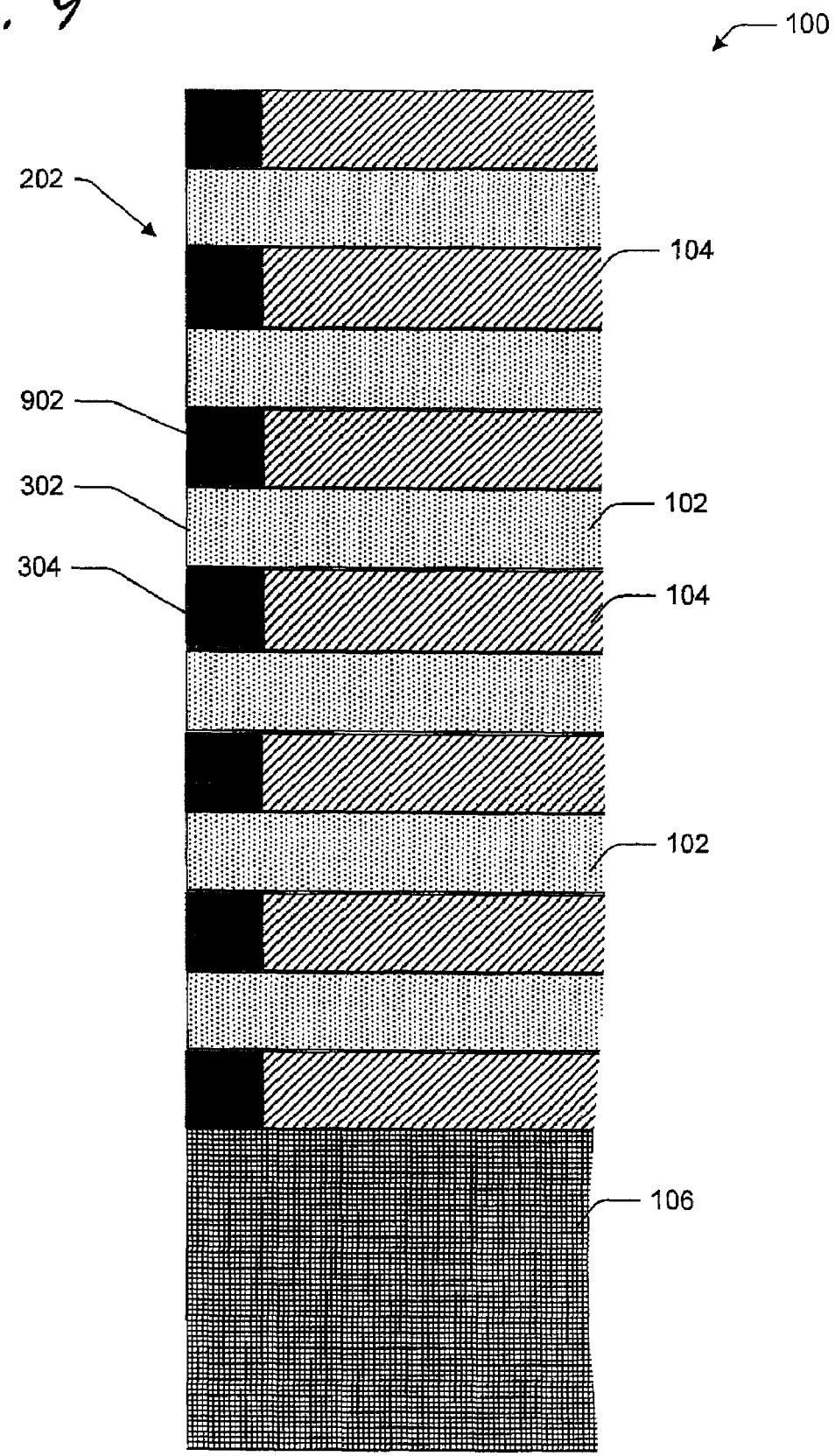
FIG. 9 illustrates a side, cross-sectional view of an exemplary superlattice having alternating layers of materials and with one set of the alternating layers being altered at a working surface.

FIG. 9 sets forth a side, cross-sectional view of examples of the superlattice 100 and the working surface 202 after the second material edges 304 have been altered. In this depiction, the material of the second material layers 104 is conductive, but has been treated such that it is no longer conductive at the working surface 202. As described above, the second material edges 304 (or the first material edges 302, depending on the implementation), can be made non-conductive by being subjected to a nitrogen or oxygen atmosphere.

In one implementation, the material of the second material layers 104 is aluminum and the material of the first material layers 102 is gold. With these being the two materials, subjecting the working surface 202 to an oxygen atmosphere will cause the first material edges 302 to be substantially unchanged, while the second material edges 304 will change from aluminum (a conductor, shown at reference 104) to aluminum oxide (a non-conductor, shown at reference 902). After a sufficient depth of change from aluminum to aluminum oxide has been reached, the second material edges 304 will be effectively non-conductive.

In some cases, however, a certain small amount of alteration to the first material edges 302 is desired. In this implementation, a small amount of alteration to the first material edges 302 can cause wires created on the first material edges 302 to not adhere as strongly as if there was no alteration.

Figure 10:
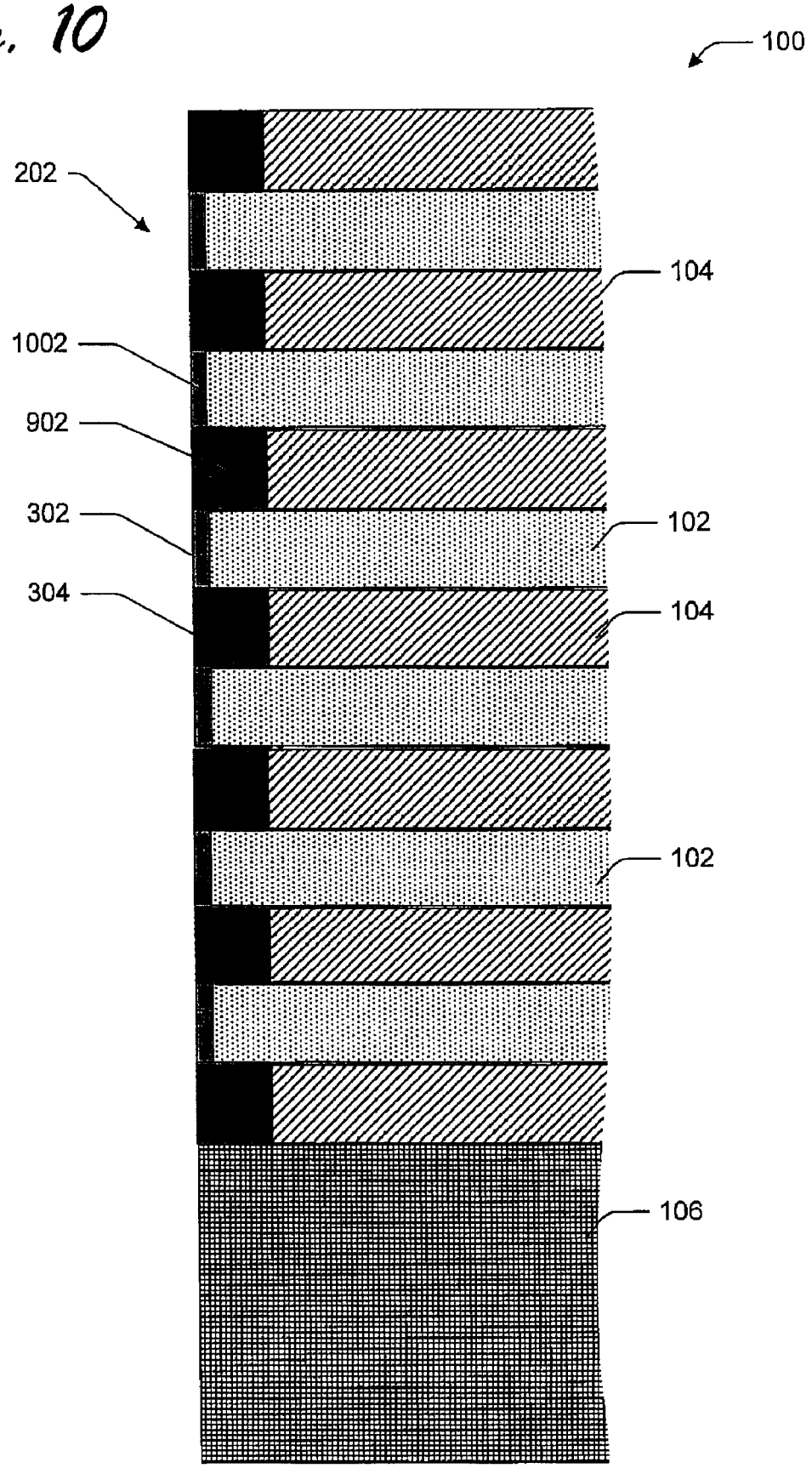
FIG. 10 illustrates a side, cross-sectional view of an exemplary superlattice having alternating layers of materials and with the materials being altered at a working surface.

FIG. 10 sets forth a side, cross-sectional view of examples of the superlattice 100 and the working surface 202 after the first and second material edges 302 and 304 have been altered. In this depiction, the material of the second material layers 104 is conductive, but has been treated such that it is no longer conductive at the working surface 202. The material of the first material layers 102 is also conductive, and has been treated at the working surface 202, but not enough to be non-conductive.

In one implementation, the material of the second material layers 104 is aluminum and the material of the first material layers 102 is tantalum. With these being the two materials, subjecting the working surface 202 to an oxygen atmosphere will cause the first material edges 302 to be changed to a small depth (compared to the depth of the second material edges 304), while the second material edges 304 will change to a comparatively large depth. The aluminum will change to aluminum oxide (shown at the reference 902 of FIG. 10). The tantalum will change to tantalum oxide (a non-conductor, shown at reference 1002). After a sufficient depth of change from aluminum to aluminum oxide has been reached, the second material edges 304 will be effectively non-conductive. The first material edges 302 can remain conductive but with desirable properties, such as lower adherence to one or more materials used to create wires for the nanowire array. The first material edges here can also be chemically etched in a solution that does not substantially etch the first material edges.

Also as part of block 610, the platform 500 can preferentially erode edges of one of the first or second material layers 102 and 104. This preferential erosion can offset the first or second material layers 102 or 104 from the working surface 202. In one implementation, preferentially eroding edges includes etching away whichever of the first or second material layers 102 and 104 is a conductor. Etching the conductive material (in this example, assume that the first material layers 102 are conductive and the second material layers 104 are non-conductive) can be performed to a certain depth. This depth can affect the eventual depth (or height) of wires of the nanowire array. This depth can also affect collection of nano-objects.

Figure 11:
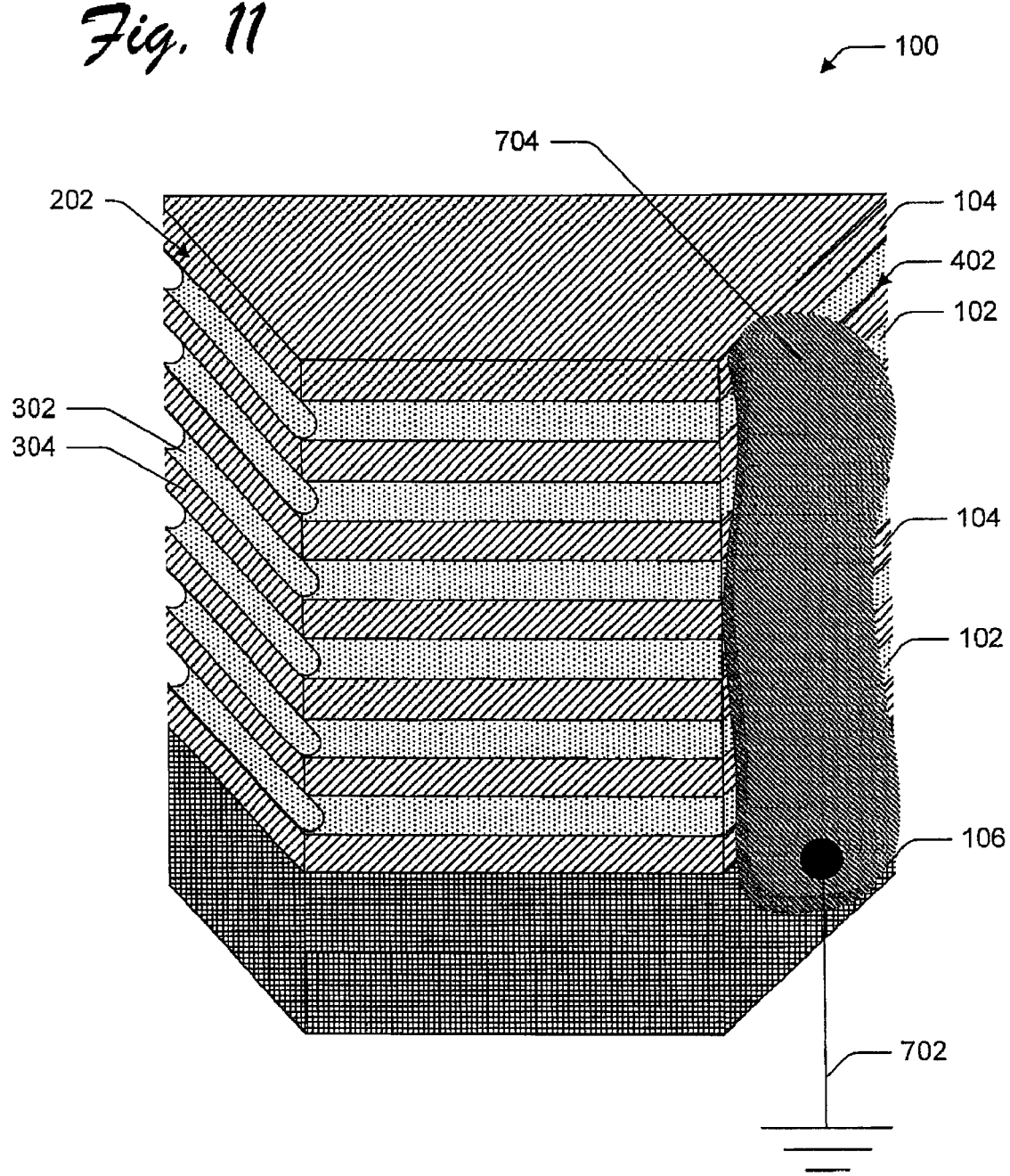
FIG. 11 illustrates a three-dimensional view of an exemplary superlattice having a corrugated working surface and an electrical connection surface in electrical communication with an electrical power sink.

FIG. 11 sets forth a three-dimensional view of examples of the superlattice 100 and the working surface 202 after the first material edges 302 have been eroded. In this depiction, the material of the first material layers 102 is conductive, but has been etched away to offset the first material edges 302 from the working surface 202. As shown in the working surface 202 of FIG. 11, this offsetting can produce furrows (or "troughs"). By so doing, the second material edges 304 form ridges relative to the troughs in the first material edges 302. As is apparent from FIG. 11, this offsetting of the second material layers 302 causes the working surface 202 to be corrugated. This corrugation can also appear, when viewed parallel to the length, to have a stepped-square, a saw-tooth, or a sine-wave appearance.

To preferentially etch, or erode, one material more than the other, the material of the first or second material layer 102 or 104 that is to be etched has a higher etch rate with respect to the etchant used.

This furrow can be useful in creating wires that are about the depth of the furrows. The furrows also have other benefits, such as protecting the wires from damage and creating a desirable wire cross-section. This cross section can be rounded on one side and approximately flat on another side. As this other side is later applied to a substrate, this flatness can be an advantage in fixing the wires to the substrate.

In one implementation, the corrugated working surface 202 of FIG. 11 is treated with a low-adhesion layer (not shown).

At block 612, in one implementation the platform 500 proceeds along the "Insulate Only" path to block 608 if part of the working surface 202 was insulated and not etched. If it was insulated and etched or otherwise preferentially exposed, the platform 500 proceeds along the "Etch and Insulate" path to block 614. The platform 500 can, however, in some implementations, proceed to block 608 after etching and insulating, prior to proceeding to block 614, to apply a low-adhesion layer to the etched and insulated working surface 202.

At block 614 the platform 500 exposes edges of the conductive material layers to ions. As part of this block 614, the platform 500 exposes the working surface 202 to ions. Those edges (either the first material edges 302 or the second material edges 304) that are conductive at the working surface 202 can attract ions. Over a period of time, collection of ions on a conductive edge will build a wire.

To attract the ions to the conductive edges, the conductive edges are at a different electrical potential or charge than the ions. This can be accomplished in various ways, including by putting the edges in electrical communication with the electrical power sink 702. In the embodiment set forth above, the electrical connection surface 402 is put in electrical communication with the electrical power sink 702. In this example, the communication is established between the electrical connection surface 402 and the working surface 202, by one or both of the first and second material layers 102 and 104 being conductive. If both layers are conductive except that one is not conductive at the working surface 202, these conductive layers provide electrical communication to the edges that are conductive at the working surface, even though not every layer is conductive at the working surface. By so doing, the first material edges 302 or the second material edges 304 (whichever is conductive at the working surface 202), can attract the ions to build wires for the nanowire array.

In one implementation, the platform 500 exposes the working surface 202 to ions by placing the working surface 202 in an ion bath. The ions in the bath can be gold, tantalum, aluminum, or nickel ions, to name a few. The material of the first material edges 302 can also be gold, tantalum, aluminum, or nickel ions, to name a few.

In another implementation, the platform 500 places the working surface 202 in an ion bath of nickel ions, which have a positive charge. In this implementation, the first material edges 302 are made up of tantalum and the second material edges 304 are made up of aluminum oxide. The material of the second material layers 104 is aluminum, but the second material edges 304 have been oxidized. In this example, wires having a nano-scale depth that are made of nickel will form at the first material edges 302 if the first material edges 302 are at a sufficiently negative potential compared with the nickel ions. Continuing this example, the first material edges 302 are at an electric potential that is lower than that of the nickel ions. This lower electric potential provided by electrical communication from the first material edges 302 through the first material layers 102 and the electrical connection surface 402 to the electrical power sink 702. Also in this example, the bath of nickel ions (not shown) is connected to an electrical power source (not shown), that keeps and/or causes them to remain positively charged.

At block 616, the platform 500 electrochemically deposits ions on the edges of the conductive layers. As shown above, the first or second material edges 302 or 304 that are conductive at the working surface 202 will attract ions if the edges are at an appropriate electrical potential compared to the ions. The platform 500 continues to deposit ions on the edges until wires of an appropriate thickness and depth are created. This thickness can be nanometer in scale or more. In one implementation, this thickness is about the same as the depth of the wires. In another implementation, this thickness is less than the depth of the wires, giving the wires a smaller thickness than depth. In still another implementation, this thickness is greater than the depth of the wires.

Figure 12:
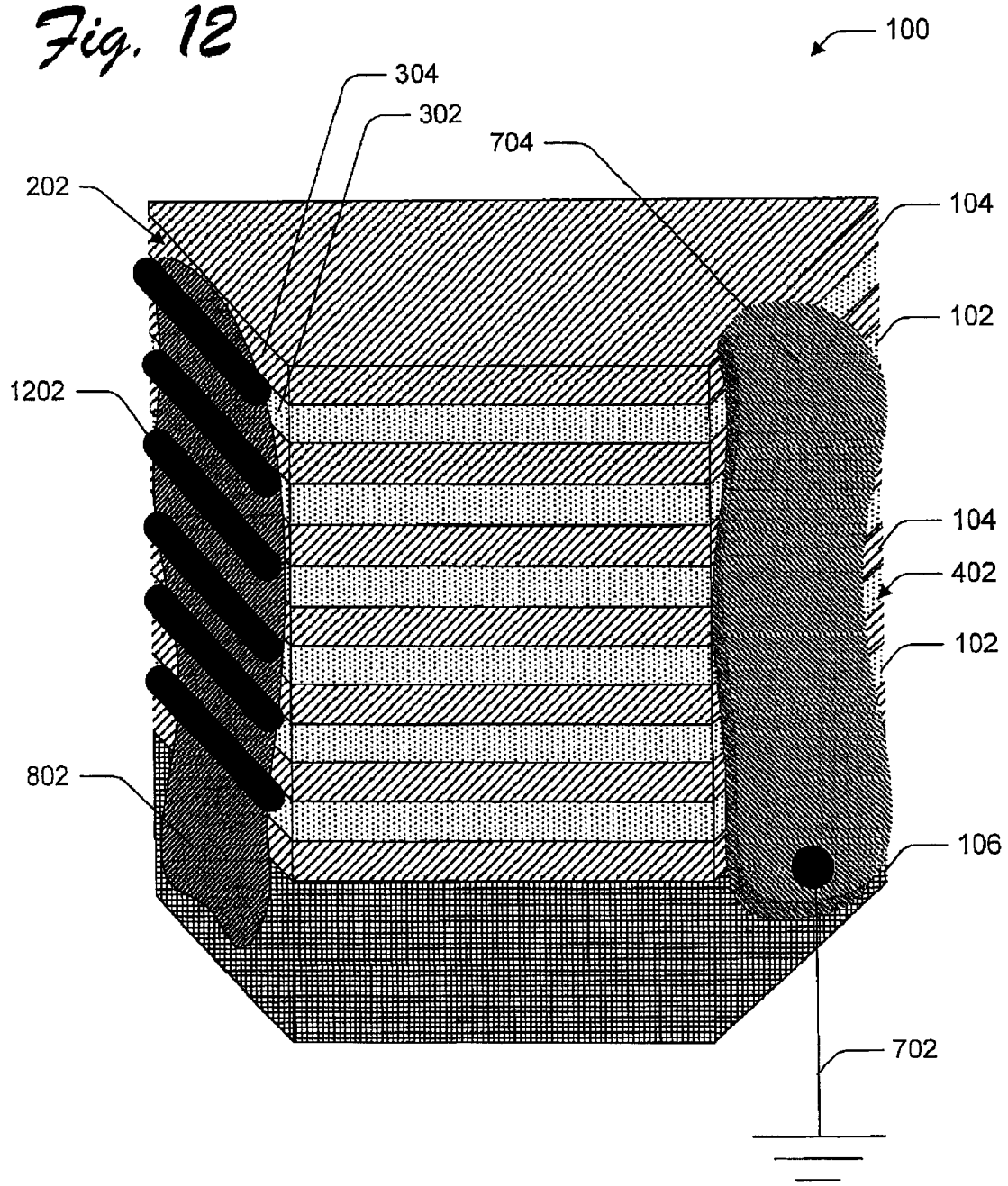
FIG. 12 illustrates a three-dimensional view of an exemplary superlattice having a working surface, the working surface having a low-adhesion layer and material present on alternating layers of the working surface, and an electrical connection surface in electrical communication with an electrical power sink.
Figure 13:
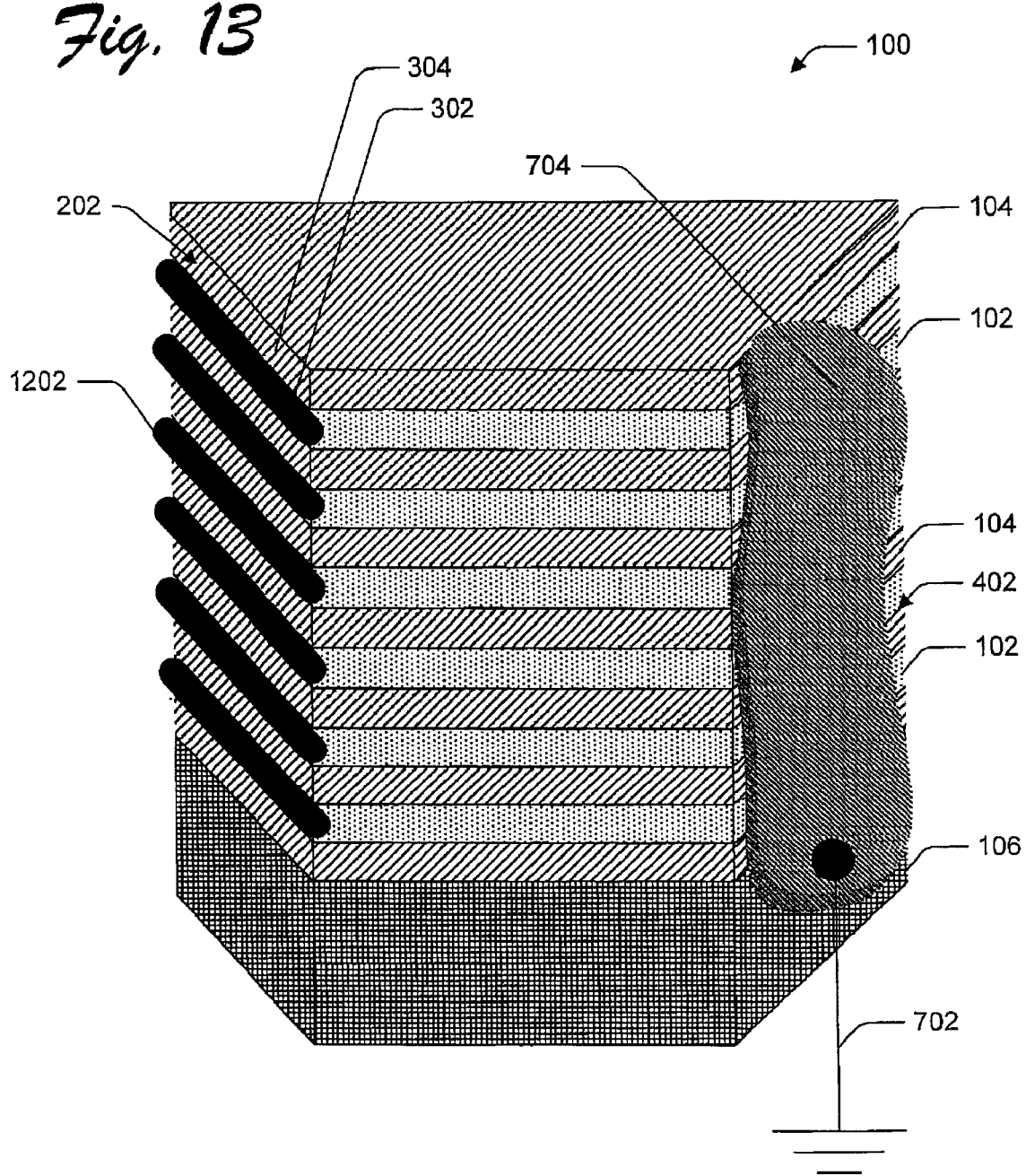
FIG. 13 illustrates a three-dimensional view of an exemplary superlattice having a corrugated working surface, the working surface having material present on alternating layers of the working surface, and an electrical connection surface in electrical communication with an electrical power sink.

FIGS. 12 and 13 show wires built up on an example of the working surface 202.

Specifically, FIG. 12 sets forth a three-dimensional view of an example of the superlattice 100 with examples of the working surface 202, the electrical connection surface 402, the electrical power sink 702, and the low-adhesion layer 802, with exemplary wires 1202 on the working surface 202. Here the wires 1202 are built over the conductive edges (here the first material edges 302) and on top of the low-adhesion layer 802.

Specifically, FIG. 13 sets forth a three-dimensional view of an example of the superlattice 100 with examples of the working surface 202 having a corrugated cross-section, the electrical connection surface 402, the electrical power sink 702, and the wires 1202. Here the wires 1202 are built up within the corrugations caused by eroding the first material layers 102 at the working surface 202.

In yet another implementation of block 616, the platform 500 places the working surface 202 in a bath with other charged objects, which include but are not limited to: ionized inorganic molecules, ionized organic molecules, ionized biological molecules, ionized polymers, charged metal, semiconductor or insulating nanoparticles, metal, dielectric, or semiconductor nano-tubes, and chemical clusters or complexes of the above. In this implementation, the electric field induced by the working surface 202 will result in electrophoretic deposition of the objects on the conductive edges of the working surface 202. This method makes it possible to form semiconductor, ceramic, organic, polymeric and other types of nanowires.

In still another implementation of block 616, the electric field generated by the working surface 202 induces a chemical reaction between dissolved chemicals and water (in a bath in which the working surface 202 is placed), on the conductive edges of the working surface 202. This results in electrolytic deposition of the reaction products on the conductive edges, forming nanowires.

At block 618, the platform 500 provides an array substrate. This array substrate acts to hold the wires formed on the working surface 202.

Figure 14:
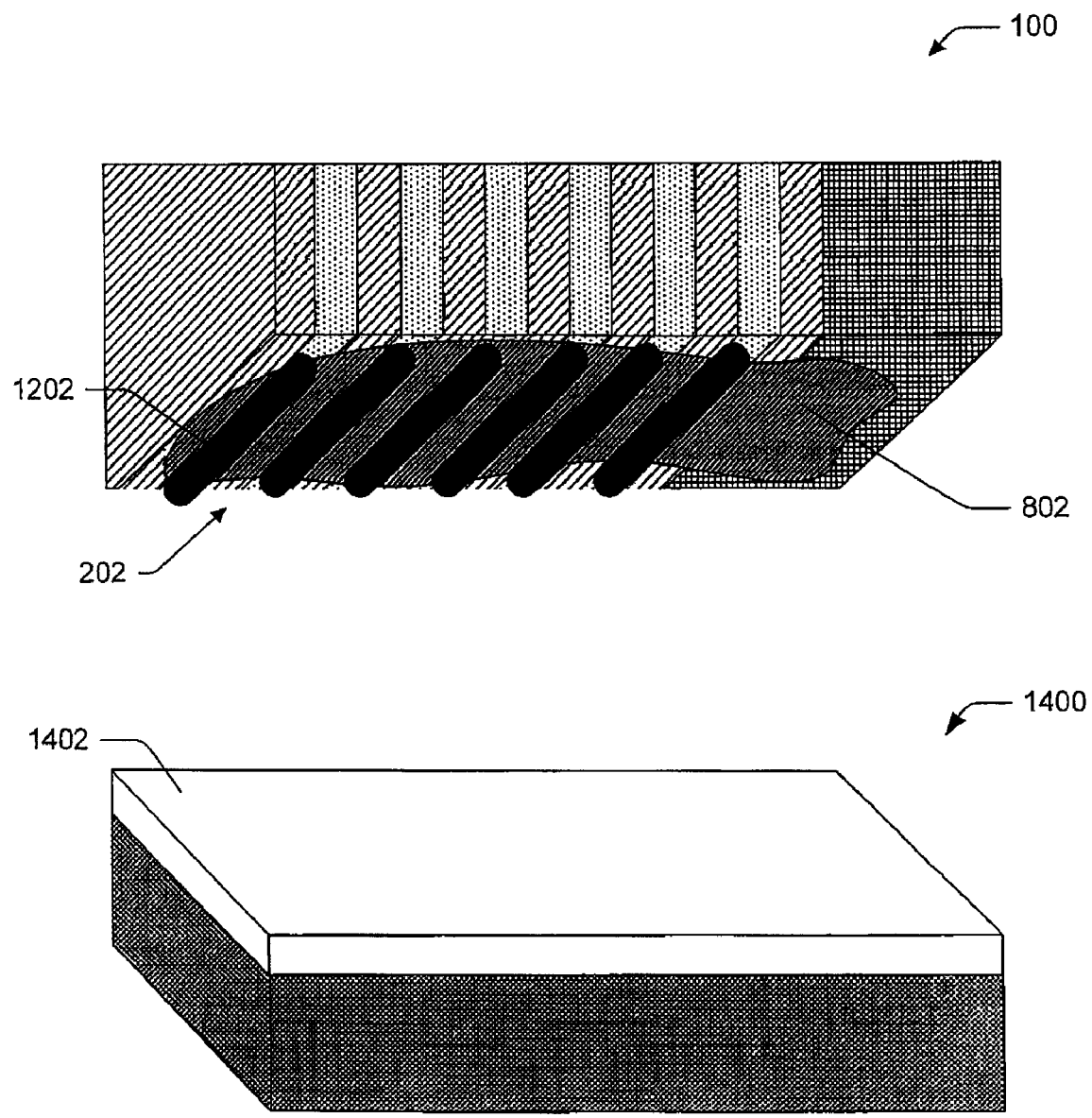
FIG. 14 illustrates a three-dimensional view of an exemplary superlattice and an exemplary array substrate, the superlattice having material on its working surface.

FIG. 14 sets forth examples of the superlattice 100, the working surface 202, the low-adhesion layer 802, the wires 1202, and an exemplary array substrate 1400. The array substrate 1400 includes a high-adhesion layer 1402. This high-adhesion layer 1402 facilitates transfer of the wires 1202 from the superlattice 100 to the array substrate 1400. The high-adhesion layer 1402 acts with an adhesion force greater than the adhesion force between the wires 1202 and the working surface 202. If there is a low-adhesion layer 802 between the wires 1202 and the working surface 202, the high-adhesion layer 1402 may be of an adhesion force that is only moderate or moderately low, but that is greater than the adhesion force of the low-adhesion layer 802 on the wires 1202.

At block 620, the platform 500 contacts the wires 1202 to the array substrate 1400. By so doing, the wires 1202 are transferred from the superlattice 100 to the array substrate 1400.

FIG. 14 shows the array substrate 1400 and the superlattice 100 prior to being placed in physical contact. After the platform 500 touches the wires 1202 to the high-adhesion layer 1402 of the array substrate 1400, the wires 1202 are transferred to the array substrate 1400.

At block 622, the platform 500 removes the superlattice 100 from the array substrate 1400, leaving the wires 1202 on the array substrate 1400.

Figure 15:
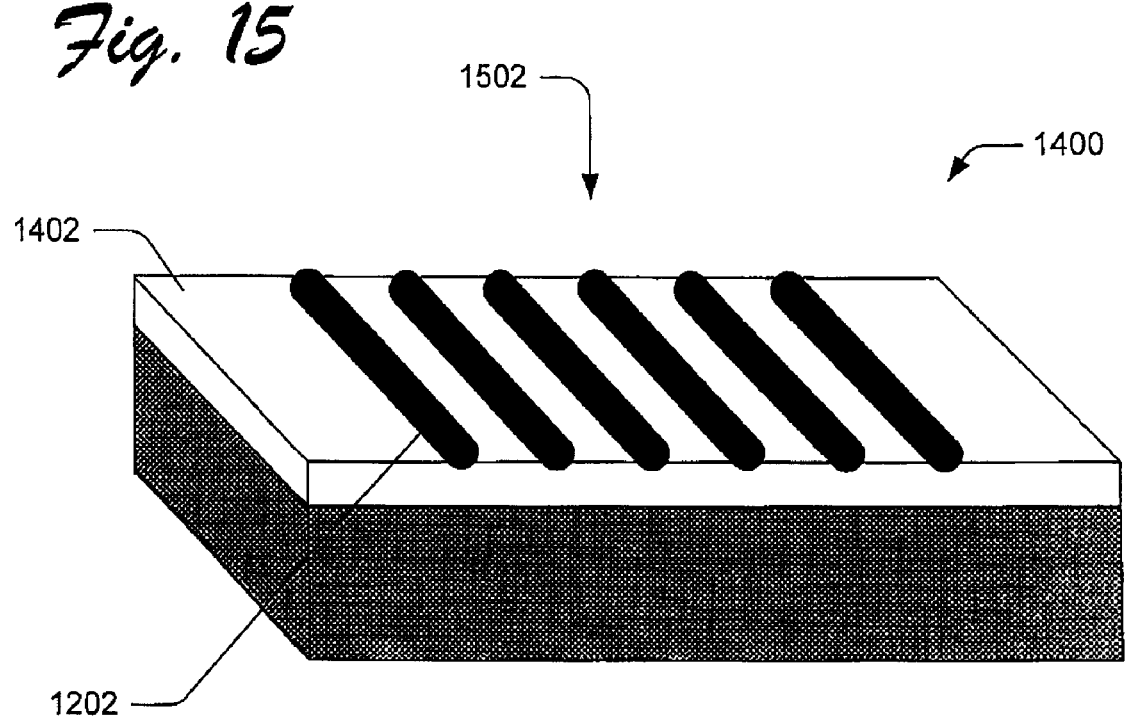
FIG. 15 illustrates a three-dimensional view of an exemplary array substrate with wires of material on one of the array substrate's surfaces.

FIG. 15 sets forth an example of the array substrate 1400 and the wires 1202 after the wires 1202 are transferred. Here the array substrate 1400 includes an exemplary array 1502 of the wires 1202.

Figure 16:
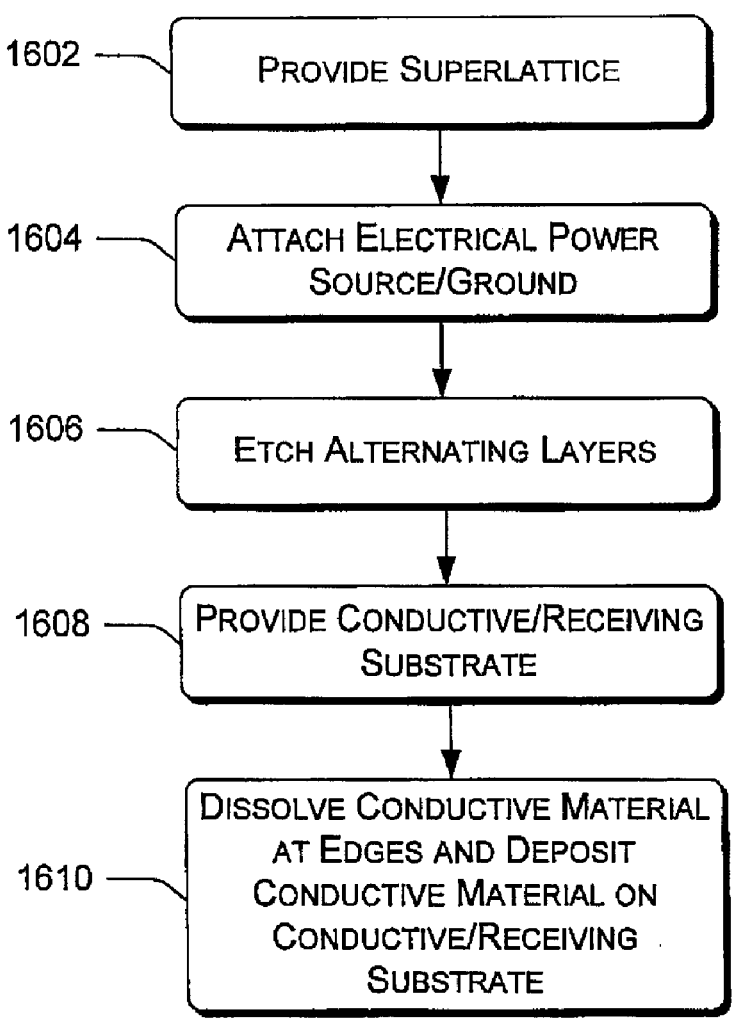
FIG. 16 is a flow diagram of an exemplary method for creating a nanowire array using ion transfer.

FIG. 16 shows an exemplary flow diagram of a process 1600 for electrochemically creating a nanowire array. This process 1600 sets forth an exemplary method for creating a nanowire array, here using electrochemical dissolution and electroplating to transfer material from the superlattice 100 to a substrate.

In another implementation (not shown), material is transferred from the substrate to the superlattice. In this other implementation, the substrate has a thin conductive film and the superlattice is used electrochemically to etch the substrate's thin conductive film into an array of nanowires. Thus, material from the substrate's thin conductive film that remains after the etching is a nanowire array.

At block 1602, the platform 500 provides the superlattice 100. This can be performed with one of the exemplary superlattices 100 set forth above. In one implementation, the platform 500 provides the superlattice 100 shown in FIG. 4, which has the working surface 202 and the electrical connection surface 402.

At block 1604, the electrical power sink 702 is attached to the electrical connection surface 402. The electrical power sink 702 can be a source or ground/sink.

At block 1606, the platform 500 erodes one of the first or second material layers 102 or 104 at the working surface 202. This erosion can be performed by etching or in other manners, similar to as set forth in the above description concerning exposing, erosion, and/or etching.

In one implementation, the platform 500 etches the second material layers 104 at the working surface 202. This creates a corrugated working surface 202, with the first material edges 302 protruding beyond that of the second material layers 304.

Figure 17:
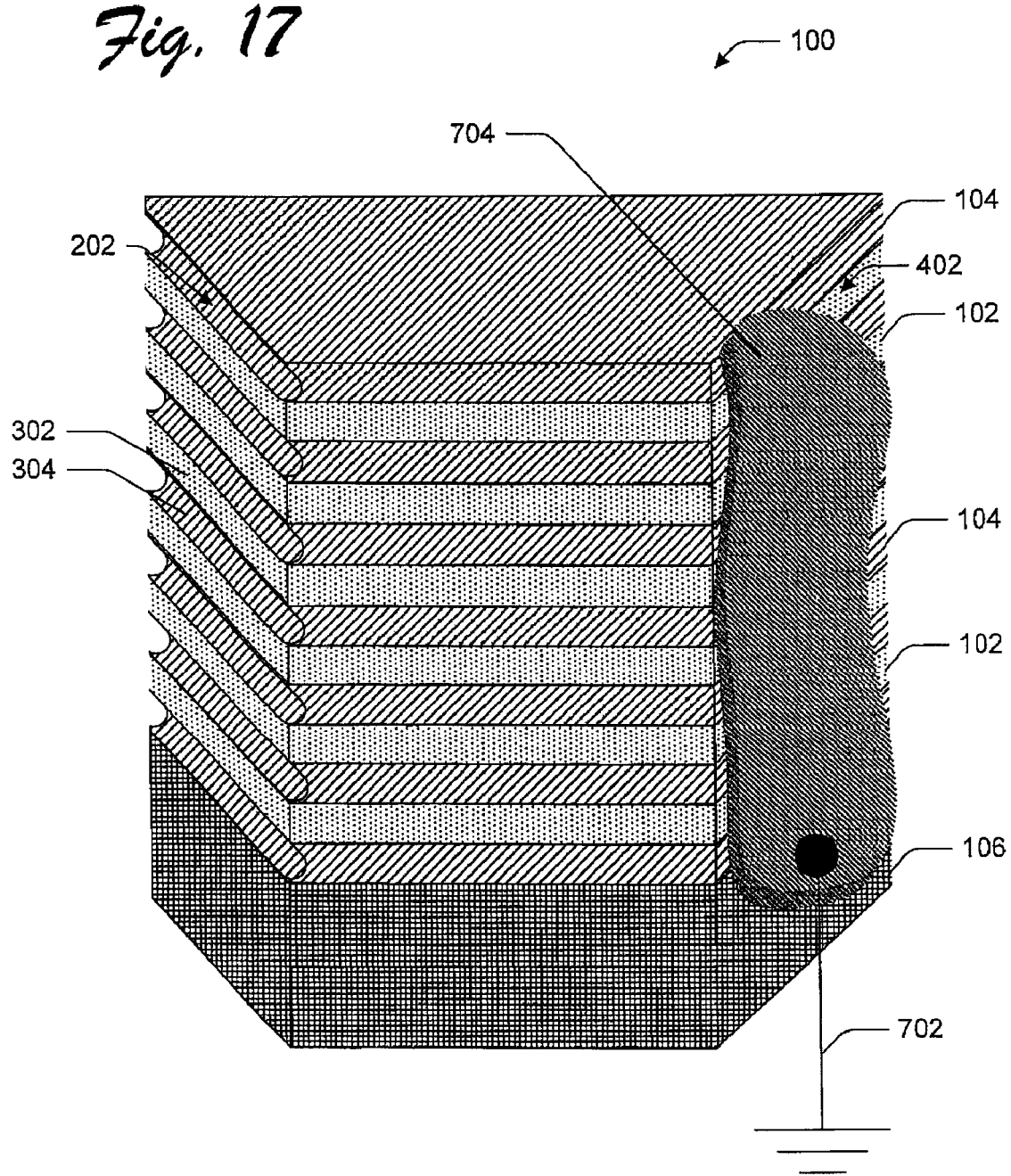
FIG. 17 illustrates a three-dimensional view of an exemplary superlattice having a working surface, the working surface having alternating layers being eroded, and an electrical connection surface being in electrical communication with an electrical power sink.

FIG. 17 sets forth a three-dimensional view of examples of the superlattice 100 and the working surface 202 after the second material edges 304 have been eroded. In this depiction, the material of the first material layers 102 is conductive, but has been exposed beyond that of the second material layers 104 by the second material layers 104 being etched away to produce furrows in the second material layers 104. This preferentially exposes the conductive material of the first material layers 102 at the working surface 202. As is apparent from FIG. 17, this etching causes the working surface 202 to be corrugated and the first material edges 302 to extend beyond the second material edges 304.

At block 1608 the platform provides a conductive receiving substrate. This conductive receiving substrate is usable to transfer material from layers of the first material layers 102 or the second material layers 104. Material can be transferred in small quantities, but sufficient to create nano-scale wires of sufficient depth from the edges of the first and/or second material edges 302 and 304.

At block 1610, the platform 500 dissolves conductive material from one or more edges of the material layers to deposit the conductive material on the conductive receiving substrate. This can be performed in various manners, including by electrochemical deposition from exposed edges of the layers to the conductive receiving substrate.

Figure 18:
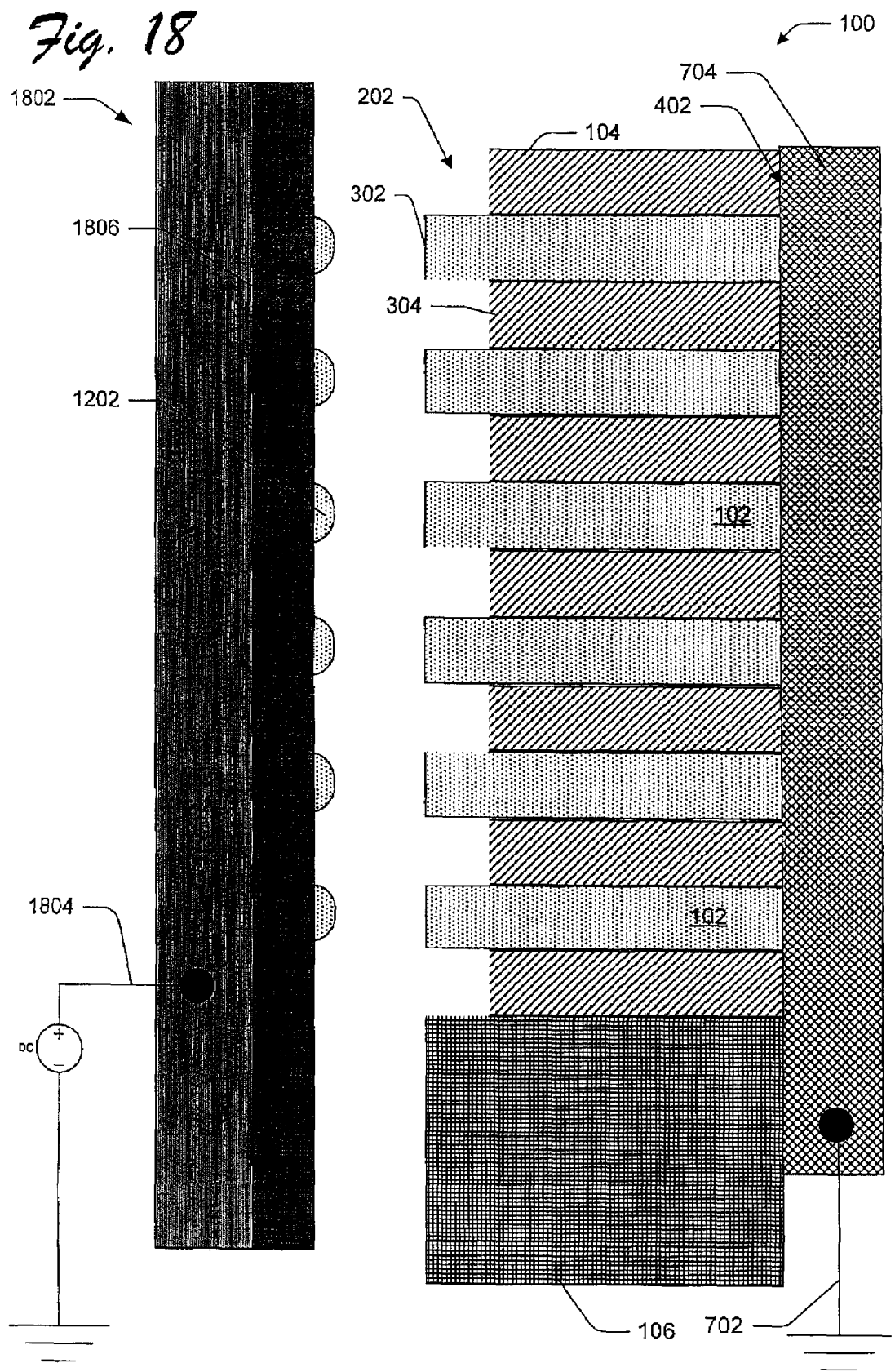
FIG. 18 illustrates a side, cross-sectional view of an exemplary superlattice having alternating layers of materials that are corrugated along a working surface, an electrical connection surface being in electrical communication with an electrical power sink, and an exemplary conductive receiving substrate being in electrical communication with an electrical power source and having one material from the working surface of the superlattice being deposited on a surface of the conductive receiving substrate.

In one implementation, shown in part in FIG. 18, material from the first material edges 302 is transferred to create wires on the conductive receiving substrate. To facilitate this transfer of material, the first material edges 302 and the conductive receiving substrate are at different electric potentials.

FIG. 18 sets forth a side, cross-sectional view of examples of the superlattice 100, the working surface 202, the electrical connection surface 402, and the electrical power sink 702, with working surface 202 having the first material edges 302 extending beyond the second material edges 304. FIG. 18 also sets forth an exemplary conductive receiving substrate 1802 in electrical communication with an electrical power source 1804. In this implementation, the conductive receiving substrate 1802 includes an insulating layer 1806 on which the wires 1202 are built.

The platform 500 can facilitate transfer of material from the first material edges 302 to the conductive receiving substrate 1802 by placing the exposed edges (here the first material edges 302) very close to the conductive receiving substrate 1802. In one implementation, the platform 500 places these within nanometers of each other. In another, within tens of nanometers of each other. The proximity affects the fineness of the deposited lines.

Also to facilitate transfer of material, the platform 500 can place the conductive receiving substrate 1802 and the first material edges 302 within an electrolyte capable of carrying ions of materials present at the first material edges 302.

In the ongoing example set forth in part in FIG. 18, the platform 500 places the first material edges 302 and the conductive receiving substrate 1802 within an electrolyte capable of dissolving the materials at the first material edges 302. In one example, the material in the first material edges 302 is nickel. In this example, the nickel is dissolved by the electrolyte to become nickel ions. These nickel ions are charged particles and are attracted to the conductive receiving substrate 1802. The nickel ions then, over time, build up on the layer 1806 of the conductive receiving substrate 1802, forming the wires 1202 of nickel. After a desired thickness and depth of the wires 1202 is achieved, the platform 500 removes the conductive receiving substrate 1802 from the working surface 202 of the superlattice 100.

The materials in the exposed first material edges 302 can include multiple materials. In one implementation, illustrated in part in FIG. 19, the first material edges 302 include four different materials.

Figure 19:
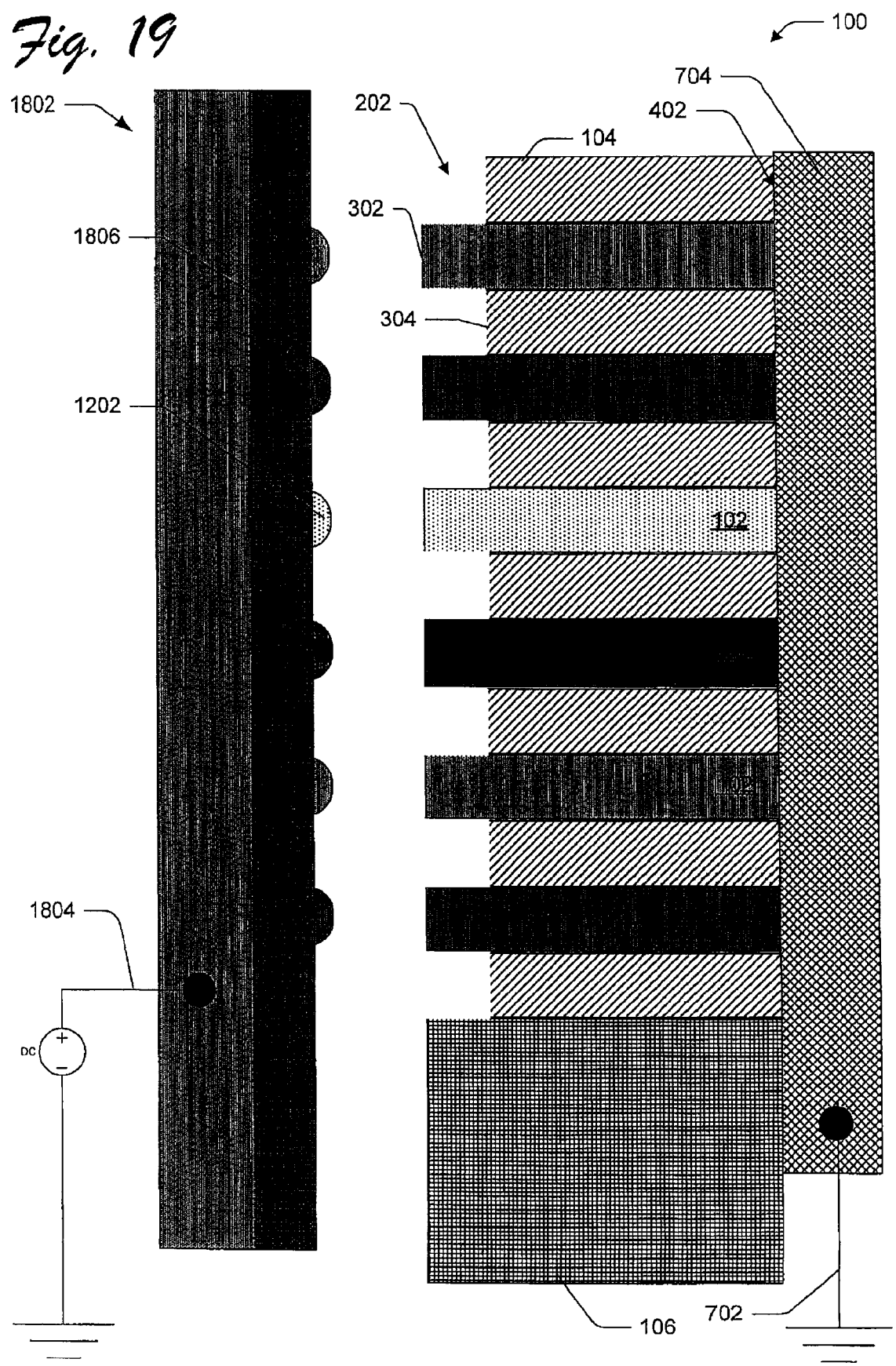
FIG. 19 illustrates a side, cross-sectional view of an exemplary superlattice having alternating layers of materials that are corrugated along a working surface with one of the alternating layers including multiple materials, an electrical connection surface being in electrical communication with an electrical power sink, and an exemplary conductive receiving substrate being in electrical communication with an electrical power source and having materials from the working surface of the superlattice being deposited on a surface of the conductive receiving substrate.

FIG. 19 sets forth a side, cross-sectional view of examples of the superlattice 100, the working surface 202, the electrical connection surface 402, and the electrical power sink 702, and working surface 202 having the first material edges 302 extending beyond the second material edges 304 and including multiple materials. FIG. 19 also sets forth an example of the conductive receiving substrate 1802 in electrical communication with the electrical power source 1804. In this implementation, the conductive receiving substrate 1802 includes the insulating layer 1804 on which the wires 1202 are built.

In this implementation, the platform 500 places the first material edges 302 within an electrolyte capable of dissolving each of the four materials. These materials can include, for example, alternating layers of the first material layers 102 of tantalum, nickel, aluminum, and gold. The platform 500 then proceeds as above.

If, however, a particular spacing is needed, an electrolyte incapable of sufficiently dissolving one or more of the four materials can be used, thereby creating wires in an array that have larger spaces between certain wires.

Nanowire arrays fabricated with the methods described herein can also be used for further processing and fabrication of other types of nanowires. In one implementation, nanowires are fabricated on top of a thin metal or semiconductor film. Then these nanowires are used as a hard mask to etch away the material of the film, thereby creating another set of nanowires made of the material of the film.

Exemplary Methods for Creating a Nano-Object Array

Figure 20:
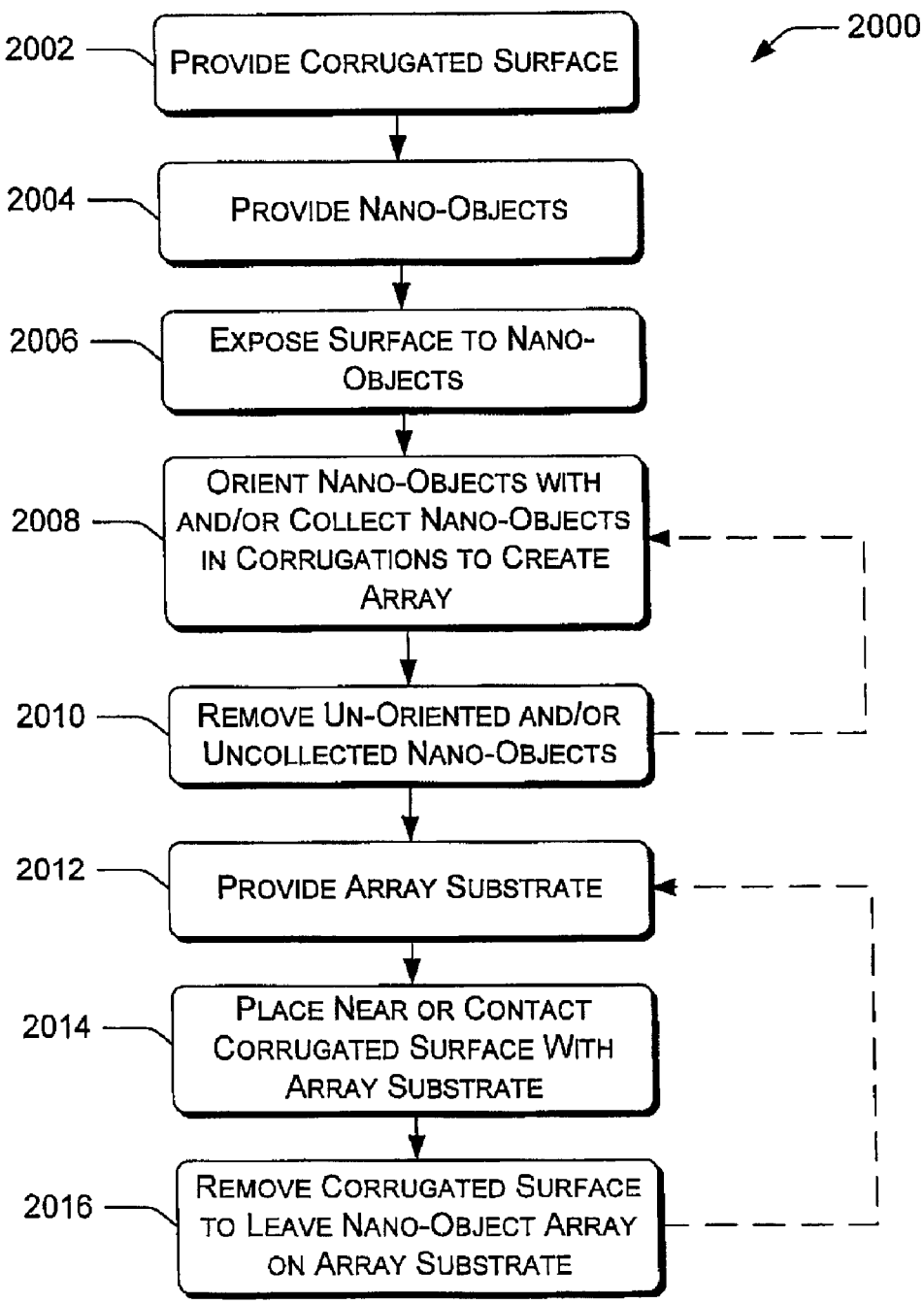
FIG. 20 is a flow diagram of an exemplary method for creating a nano-object array.

FIG. 20 shows an exemplary flow diagram for a process 2000 for creating a nano-object array. Nano-objects can function as conductors, insulators, semiconductors, and structural bodies, making the array useful in many different applications.

Nano-objects are three-dimensional, substantially straight physical objects with two dimensions between 0.7 and 100 nanometers and a third dimension between 100 nanometers and ten centimeters. Thus, nano-objects are long, thin objects. Nano-objects can include many different materials and structural arrangements of materials.

At block 2002 the platform 500 provides a corrugated surface. This corrugated surface includes troughs and ridges making up the corrugation of the surface. The troughs and ridges can be of varying thicknesses, with the troughs' thickness being nanometer in scale (between 0.7 and one hundred nanometers) and the ridges being from nanometer to meso-meter or macro-meter in scale. The length of the troughs and ridges can be from about 100 nanometers to centimeter in scale, with the length dimension being substantially larger than the thickness dimension.

Various implementations of the superlattice 100 will be used to aid in the discussion of the process described below. These implementations of the superlattice 100 are examples of a structure having a corrugate surface that is usable in the below-discussed process. Other structures, surfaces, and superlattices can be used; these exemplary corrugated surfaces and superlattices are not intended to be limiting on the scope of the below-described process, but instead are intended to aid the reader in understanding this process.

In one implementation of the block 2002, the corrugated surface provided includes any example of the superlattice 100 having corrugations and created or mentioned as part of the process 600. Thus, the block 2002 can include implementations of the blocks 602 to 612 of the process 600 that results in a corrugated surface.

Figure 21:
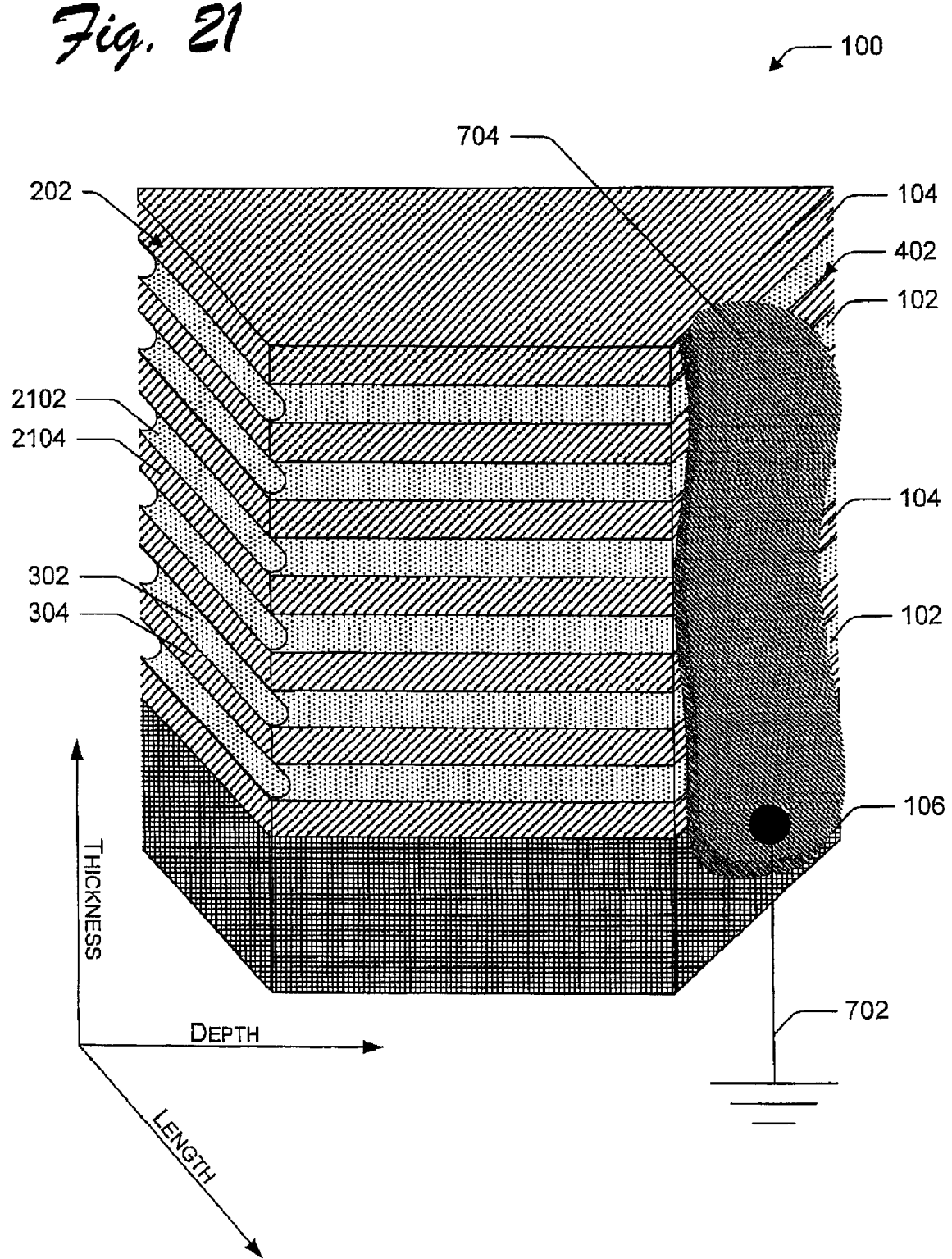
FIG. 21 illustrates a three-dimensional view of an exemplary superlattice having a corrugated surface with troughs and ridges, an electrical connection surface in electrical communication with an electrical power sink, and thickness, depth, and length dimensions.

FIG. 21 sets forth a three-dimensional view of an example of the superlattice 100 with a corrugated example of the working surface 202. This example of the superlattice 100 has the electrical connection surface 402, the electrical connection surface 402 being in electrical communication with the electrical power sink 702.

Also in this exemplary superlattice 100, the material of the first material layers 102 is conductive, but is offset from the working surface 202 to produce troughs 2102 in the first material layers 102. This exposes the second material layers 104 as ridges 2104 in the working surface 202. These troughs 2102 will be used by the platform 500 to orient and/or collect nano-objects, described below.

The corrugated working surface 202 shown in FIG. 21 can include a semi-circular cross-section for the troughs 2102 (shown) and plateau cross-sections for the ridges 2104 (shown), but can also include cross-sections that appear, when viewed parallel to the length, to have a stepped-square, a saw-tooth, a sine-wave, or a shallow-notch appearance.

In one implementation, the troughs 2102 are an offset example of the first material edges 302 and the ridges 2104 are a corresponding example of the second material edges 304.

At block 2004, the platform 500 provides nano-objects. These nano-objects can be made up of many different kinds of materials, such as inorganic molecules, organic molecules, biological molecules, metal, semiconductor, or insulating nano-particles. They can also have various kinds of shapes and structures. They can include, for instance, single- and multi-wall carbon nanotubes of various chiralities; boron-nitride nanotubes; molybdenum disulfide nano-tubes; bundles and ropes of nanotubes; solid or hollow nanowires made of metals, semiconductors, conductive oxides, conductive polymers, or other conductive materials; insulating nano-rods; and conductive or insulating nano-needles.

These nano-objects have a length, a thickness, and a depth but are substantially longer than they are thick or deep.

In one implementation, the thickness and depth of the nano-objects is less than the thickness of the troughs 2102 so that the nano-objects can be collected within the troughs 2102.

These nano-objects can be substantially straight or less straight but flexible enough to conform to the troughs 2102.

In one implementation, the nano-objects are nano-tube complexes. These complexes are moderately straight (have some curves), flexible, and have a hollow cross-section. The nano-tubes can comprise a polymer, including those with carbon, such as polyvinyl pyrrolidone and polystyrene sulfonate, or otherwise. The nano-tubes can also comprise non-carbon compounds, such as boron-nitride or molybdenum disulfide.

In one implementation of block 2004, the platform 500 provides charged nano-objects by ionizing them within a bath. Having the nano-objects charged can aid in orienting with and/or collecting them in the troughs 2102, discussed below.

Figure 22:
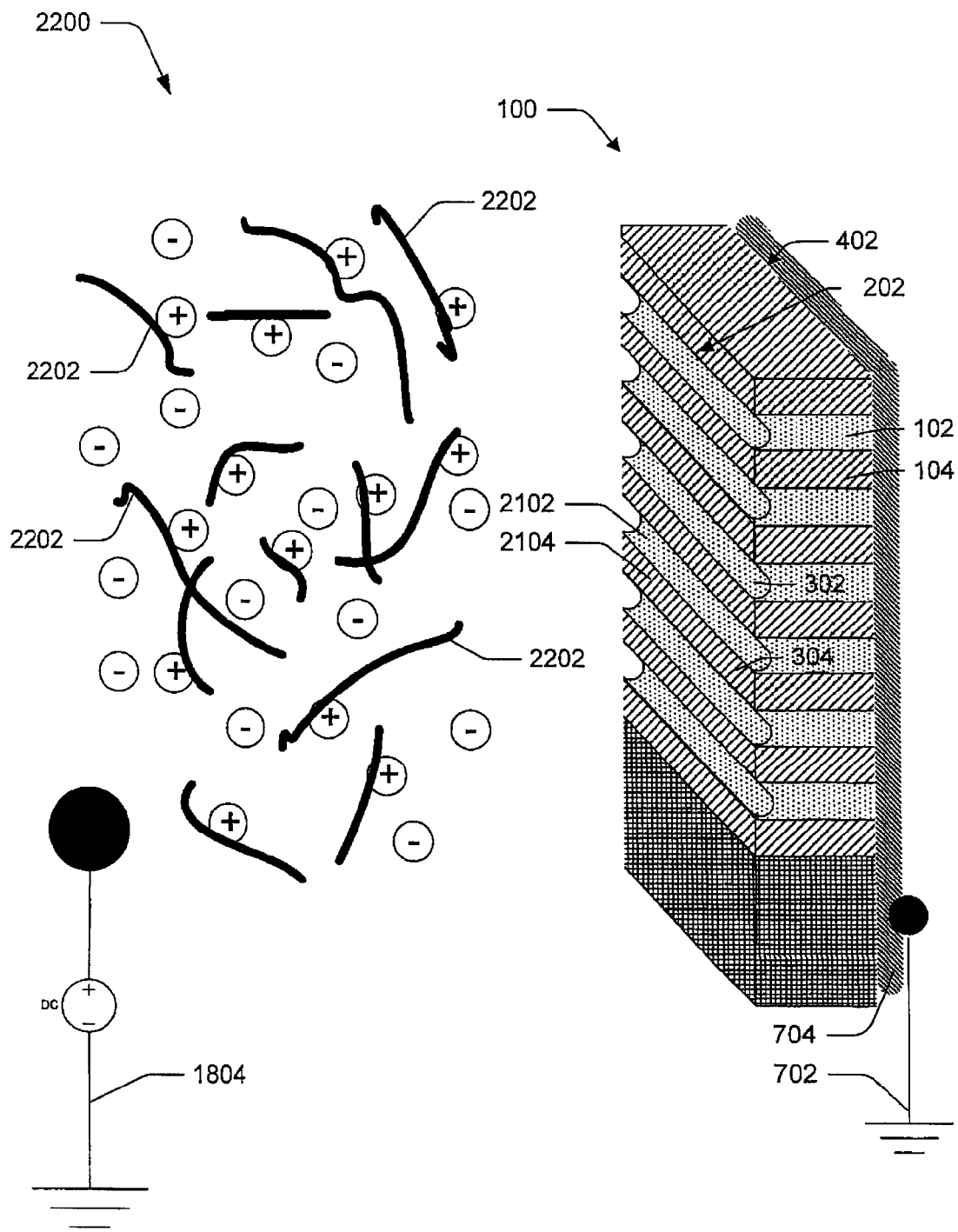
FIG. 22 illustrates a three-dimensional view of an exemplary superlattice having a corrugated surface with troughs and ridges, an electrical connection surface being in electrical communication with an electrical power sink, and an exemplary bath in electrical connection with an electrical power source and containing exemplary ionized nano-objects.

FIG. 22 sets forth a three-dimensional view of an example of the superlattice 100 with a corrugated example of the working surface 202 having the troughs 2102, the ridges 2104, and being in electrical connection via the connection surface 402 and the conductive connection material 704 with the electrical power sink 702.

FIG. 22 also sets forth a bath 2200, having charged examples of nano-objects 2202, and the electrical power source 1804.

At block 2006, the platform 500 exposes the corrugated surface to the nano-objects.

In one implementation, the platform 500 exposes the working surface 202 (and thus the troughs 2102 and the ridges 2104) of the superlattice 100 to the charged nano-objects 2202 by placing the working surface 202 within the bath 2200 containing the charged nano-objects 2202.

At block 2008, the platform 500 orients with and/or collects nano-objects in the troughs 2102 of the working surface 202.

In an example of the above implementation, the platform 500 exposes the working surface 202 to the charged nano-objects 2202 and charges the troughs 2102 at the working surface 202 to attract the charged nano-objects 2202. Over a period of time, collection of the charged nano-objects 2202 can build an array of the nano-objects 2202.

In a related implementation of blocks 2004, 2006, and 2008, the platform 500 provides the charged nano-objects 2202 by ionizing them within the bath 2200, exposes the working surface 202 of the superlattice 100 by placing it within the bath 2200, and then collects the charged nano-objects 2202 in the troughs 2102 of the working surface 202 to create an array.

In greater detail, this implementation, with regard to block 2008, electrophoretically collects the charged nano-objects 2202 to build an array by attracting ions of nano-objects to conductive offset edges/troughs of a corrugated surface. To do so, the platform 500 can create an electrical potential at the troughs 2102 relative to the charged nano-objects 2202. This can be accomplished in various ways, including by putting the troughs 2102 in electrical communication with the electrical power sink 702. In the embodiment set forth above and described in part in FIG. 22, the electrical connection surface 402 is put in electrical communication with the electrical power sink 702. In this example, the communication is established between the electrical connection surface 402 and the working surface 202, by the troughs 2102 being conductive (through the first material layers 102 being conductive). If the second material layers 104 are also conductive, they are not substantially conductive at the working surface 202 or at the exposed parts of the ridges 2104, so that the charged nano-objects 2202 are collected in and/or oriented with the troughs 2102. The ridges 2104 can be made non-conductive in the various ways set forth above. Also in this example, the bath 2200 is connected to the electrical power source 1804 to keep and/or cause the nano-objects 2202 to remain charged.

In another implementation of blocks 2004, 2006, and 2008, the platform 500 provides the charged nano-objects 2202 by charging a solution containing nano-objects and interfering ions. The interfering ions are spatially distributed to the troughs 2102. These interfering ions can restrict a size of a spatial region within which an electric field is non-zero near the troughs 2102. The size of the spatial region within which the electric field is non-zero can be calculated by its Debye length, which is:

$$L_D = \sqrt{\frac{\varepsilon_0 \varepsilon_{el} kT}{|q|^2 \sum n_i z_i^2}}$$

Here $\varepsilon_0 = 8.85 \cdot 10^{-12}$ F./m is the permittivity of free space, $\varepsilon_{el}$ is the relative permittivity of the liquid solvent without ions, $|q| = 1.6 \cdot 10^{-19}$ C. is the elementary charge, $k = 1.38 \cdot 10^{-23}$ J/K. is the Boltzmann constant, T is the absolute temperature (room temperature is about T=298K.), and $n_i$ is the equilibrium volume concentration of ions with valence $z_i$. Thus, the Debye length is a function of pH of the solution, ionic strength, and ionic charge. As an example, in case of monovalence acidic solution with pH=5.5 the Debye length, $L_D$, is about 200 nanometers. The platform 500 can control pH to restrict the size of the spatial region within which the electric field is non-zero.

The nano-objects that contact the restricted spatial region within which the electric field is non-zero are then polarized if the nano-objects are at least partially conductive. Once polarized, the nano-objects can be attracted to and collected in and/or oriented with the troughs 2102. This way to restrict the size of the electric field can reduce a number of partially collected and oriented nano-objects. It can also increase how many of the nano-objects (such as the charged nano-objects 2202) are collected within the troughs 2102.

Also, a small alternating current signal may be applied to the bath whenever the nano-objects are charged or polarized. This small signal creates an additional, oscillating force on the charged nano-objects 2202 (such as the polarized nano-objects near the troughs 2102). This oscillating force can enable the nano-objects that are near, but not fully collected within the troughs 2102, to settle into the troughs 2102. Certain of the polarized nano-objects, for instance, may be partially outside of the troughs 2102, may be lying partly on the ridges 2104, or the like. These states are only meta-stable; the oscillating force can enable these certain nano-objects to settle into a more stable position within the troughs 2102.

As part of the block 2004 and/or 2008, the bath 2200 can be created or maintained to optimize the behavior of the nano-objects 2202. The behavior of the nano-objects 2202 can be optimized by adjusting the temperature, geometry of the bath, flow, ionic strength, and pH of the bath 2200.

An ionic strength and pH of the bath 2200 affects the ionization of the nano-objects 2202 in a water solvent. Thus, a lower pH is more acidic, and can cause certain types of nano-objects 2202 to be correspondingly charged. A pH of the bath 2200 can be between zero and fourteen, such as between three and ten.

The temperature of the bath 2200 can be adjusted, based on the type of solute (e.g., the nano-objects 2202) and solvent within the bath 2200. For a solution of water and nano-objects of carbon polymer nano-tube complexes, for instance, a temperature of fifteen to thirty degrees Celsius can be used. For a solution having a solvent of alcohols or molten salts, however, temperatures from about minus forty degrees Celsius to about 150 degrees Celsius can be used.

The geometry (and corresponding flow) of the bath 2200 can be adjusted to aid in orienting the long dimension (the length) of the nano-objects 2202 with the length dimension of the troughs 2102 and the ridges 2104 of the working surface 202.

Figure 23:
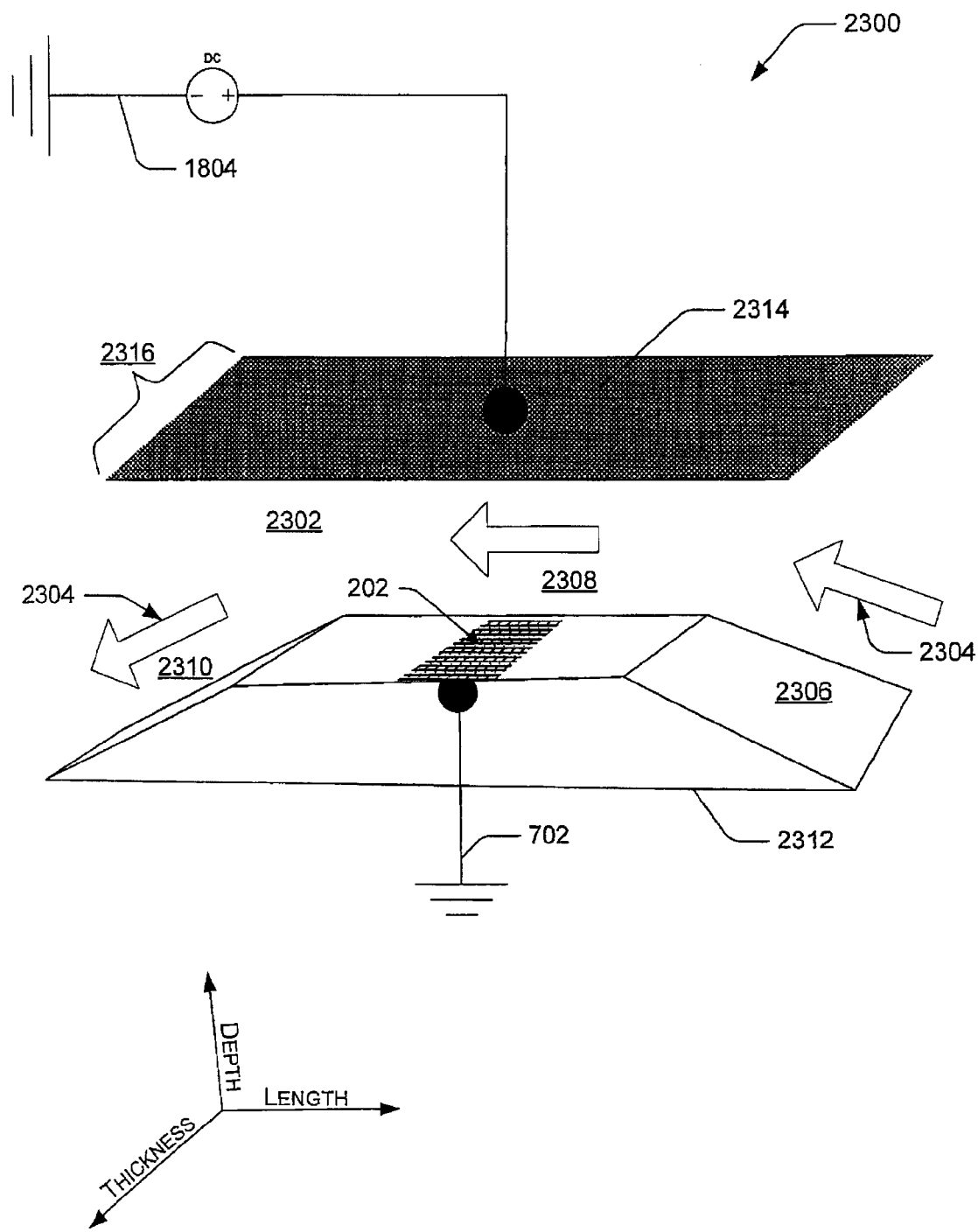
FIG. 23 illustrates a three-dimensional view of an exemplary directed flow bath having a bath platform holding an exemplary superlattice, a shelf connected to an electrical power source, and having thickness, depth, and length dimensions.

FIG. 23 shows a directed flow bath 2300, which is an example of the bath 2200. The directed bath 2300 has a channel 2302 flowing in a direction 2304. The channel 2302 has an approach region 2306, a collection region 2308, and an exit region 2310. The superlattice 100 resides within a bath platform 2312, thereby exposing the working surface 202 in the collection region 2308. Above the working surface 202 is a shelf 2314 that directs, in conjunction with the bath platform 2312, the flow within the channel 2302. This shelf 2314 and the directed bath 2300 allow a flow having a particular width (along the thickness dimension), referenced with 2316. The shelf 2314 can include the electrical power source 1804 near to the working surface 202 but separated by the flow of solution (not shown). The electrical power source 1804 can also be placed within the solution and near to the working surface 202. The working surface 202 is shown in electrical communication with the power sink 702.

A distance between the shelf 2314 and the working surface 202 can affect how easily the nano-objects 2202 are oriented and collected in the troughs 2102. By limiting this distance (the height of the collection region 2308) the physical characteristics of the flow of the fluid in the bath 2300 can orient the long, thin nano-objects 2202 parallel with the direction 2304 of the flow in the channel 2302. This orienting can make easier further orienting and collection of the nano-objects 2202 in or with the troughs 2102.

In one implementation of the directed bath 2300, the height of the channel 2302 at the collection region 2308 (a distance between the shelf 2314 and the working surface 202) is between about 0.1 to about one millimeter. In another implementation, the distance in region 2308 is between about one micron to about ten centimeters.

The bath and shelf width 2316 can be adjusted based on the fluid characteristics of the directed bath 2300. If the width 2316 is too low, the nano-objects 2202 may not orient as easily with the troughs 2102, especially at the troughs 2102 residing far from a center of the working surface 202.

In one implementation of the directed bath 2300, the bath and shelf width 2316 is between one and 100 times the thickness of the working surface 202. FIG. 23 shows the width 2316 being slightly wider than the working surface 202. In another implementation, the width 2316 is two to five times wider than the thickness of the working surface 202.

A velocity or rate of flow ("flow rate") of the solution (which contains the nano-objects 2202) can also be adjusted to optimize orientation and collection of the nano-objects 2202 with or in the troughs 2102 of the working surface 202. The flow rate should be such that laminar flow occurs in the collection region 2308 during orientation and collection of the nano-objects.

In one implementation, the flow rate is adjusted to keep a Reynolds number below thirty to prevent turbulent flow. The Reynolds number is a dimensionless fluid parameter, roughly equal to a ratio of inertial and viscous forces in a fluid. When a Reynolds number is below thirty, a fluid has no turbulent (only laminar) flow. When a Reynolds number is above thirty, a fluid has some turbulent flow. The Reynolds number ("Re") can be determined by finding the characteristic dimension of the channel 2302 (here at the collection region 2308), called "D", the velocity of the solution at the collection region 2308, called "V", the density of the solution, called "ρ", and the viscosity of the solution, called "η". Specifically, $$\text{Re} = \frac{V \cdot D \cdot \rho}{\eta}.$$

With this information Re is determinable. D is determinable, primarily based on the distance between the working surface 202 and the shelf 2314. The velocity, V, is adjustable and determinable in manners well known in the art of fluid mechanics. The density of solution and its viscosity can also be adjusted, including by using known additives.

In laminar flow, the fluid velocity profile is not uniform across the channel 2302. Instead, the velocity of the solution is lower near walls (such as the floor of the collection region 2308) and higher in the center. Because of this, a long, thin nano-object in the solution experiences a stronger drag on its end closer to the center of the channel 2302 than the collection region 2308, causing the nano-object to align along the direction 2304 of the flow path. When the troughs 2102 and the ridges 2104 of the working surface 202 are aligned with the direction 2304 of the flow path, the nano-objects align (e.g., orient) with the troughs 2102 and the ridges 2104. To further aid in this alignment, trenches running parallel to the troughs 2102 and the ridges 2104 can be added to the approach region 2306 and the collection region 2308.

As part of the block 2002, 2004, and/or 2008, the voltage difference/potential of the bath 2200 (or the directed bath 2300) can be adjusted through the power sink 702 and the electrical power source 1804 to affect the behavior of the nano-objects 2202. The voltage difference used is dependent on a decomposition potential of the solution. The voltage difference should not exceed this decomposition potential. Other factors include an affect on the nano-objects 2202; some materials and structures of the nano-objects 2202 are more sensitive to voltage differences than others.

In one implementation, when using water as the solvent for the solution in the bath 2200, the voltage difference is between about one and ten volts.

In another implementation, the voltage difference between the power sink 702 and the power source 1804 is between 0.001 and 100 volts, with the voltage chosen based on the materials and structure of the nano-objects 2202 and the solvent used in the bath 2200.

In this implementation of block 2008, the platform 500 electrophoretically deposits nano-objects 2202 in the troughs 2102 of the first materials layers 102 at the working surface 202. As shown above, the troughs 2102 that are conductive at the working surface 202 will attract nano-objects 2202 if the troughs 2102 are at an appropriate electrical potential compared to the nano-objects 2202. The platform 500 continues to deposit nano-objects 2202 on the edges until an array of the nano-objects 2202 is created.

Figure 24:
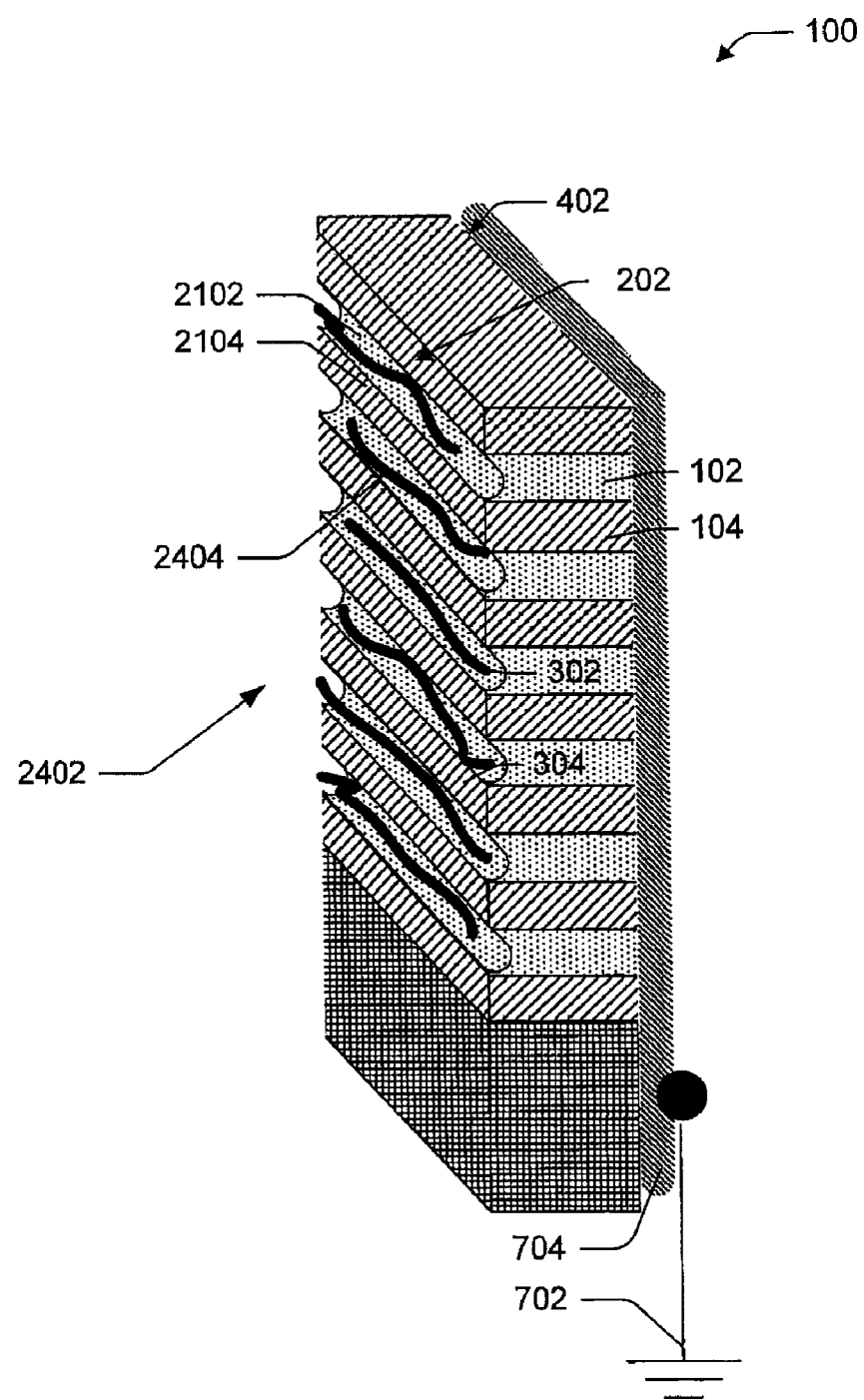
FIG. 24 illustrates a three-dimensional view of an exemplary superlattice having a corrugated surface with troughs in the surface containing nano-objects making up an exemplary array, and an electrical connection surface in electrical communication with an electrical power sink.

FIG. 24 shows an array 2402 of nano-objects 2404. The nano-objects 2404 are oriented with and collected within the troughs 2102 of the example of the superlattice 100.

Specifically, FIG. 24 sets forth a three-dimensional view of an example of the superlattice 100 with examples of the working surface 202 having a corrugated cross-section with the troughs 2102 and the ridges 2104, the electrical connection surface 402, the electrical power sink 702, and the nano-objects 2404.

At block 2010, the platform 500 removes un-oriented and/or uncollected nano-objects from the working surface 202, if needed. In some implementations of block 2008, some of the nano-objects are not fully oriented or collected within the troughs 2102 of the working surface 202. In this case the platform 500 removes these un-arrayed nano-objects.

In other cases, some of the nano-objects are un-oriented and/or uncollected and some of the troughs 2102 are not fully filled with the nano-objects. In these cases the platform 500 can remove the un-oriented and/or uncollected nano-objects and then return to block 2008 to collect and/or orient additional nano-objects.

Figure 25:
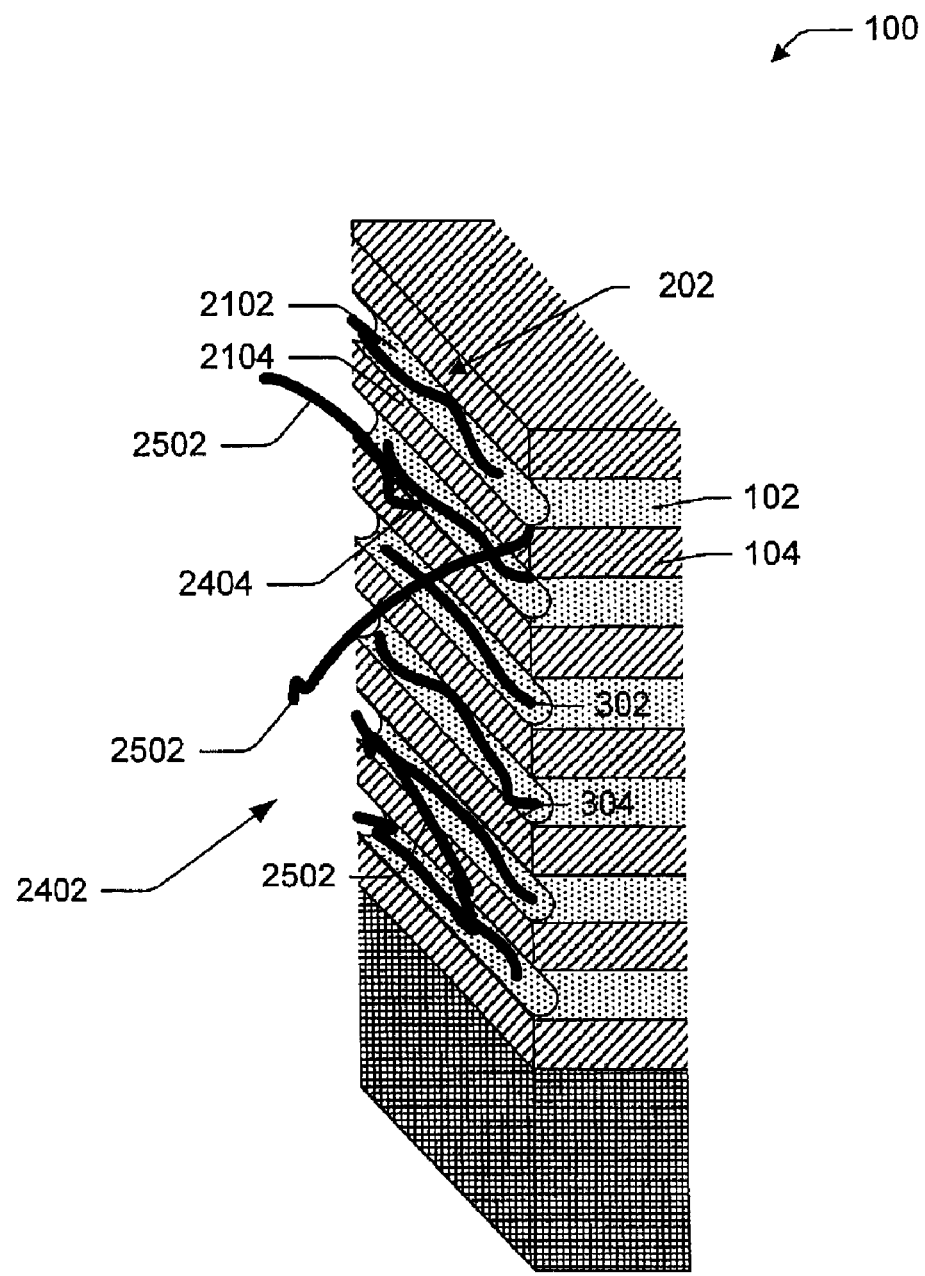
FIG. 25 illustrates a three-dimensional view of an exemplary superlattice having a corrugated surface with troughs in the surface containing nano-objects making up an exemplary array and un-arrayed nano-objects not making up the exemplary array.

FIG. 25 shows the array 2402 of the nano-objects 2404 and un-arrayed nano-objects 2502. The un-arrayed nano-objects 2502 are not oriented with and not fully collected within the troughs 2102 of the example of the superlattice 100.

In one implementation of block 2010, in cases where the nano-objects are laminarly flowed along the troughs 2102, the platform 500 introduces turbulent flow outside of the troughs 2102 to remove the un-arrayed nano-objects 2502 that are not collected within the troughs 2102. Turbulence in the flow introduces mixing, which facilitates removal of nano-objects not within the troughs 2102. Turbulence can be introduced by adding gas bubbles into the flow. Turbulence can also be introduced by increased the fluid viscosity or the velocity of the fluid in the flow. Because turbulence is dependent on the geometry of the troughs 2102, the flow can be made turbulent outside of the troughs 2102 but not in the troughs 2102.

In another implementation of block 2010, the platform 500 agitates the un-arrayed nano-objects 2502. The platform 500 can "shake off" the un-arrayed nano-objects 2502 using ultrasonic energy, for instance.

At block 2012, the platform 500 provides an array substrate. This array substrate is used to hold the array 2402.

Figure 26:
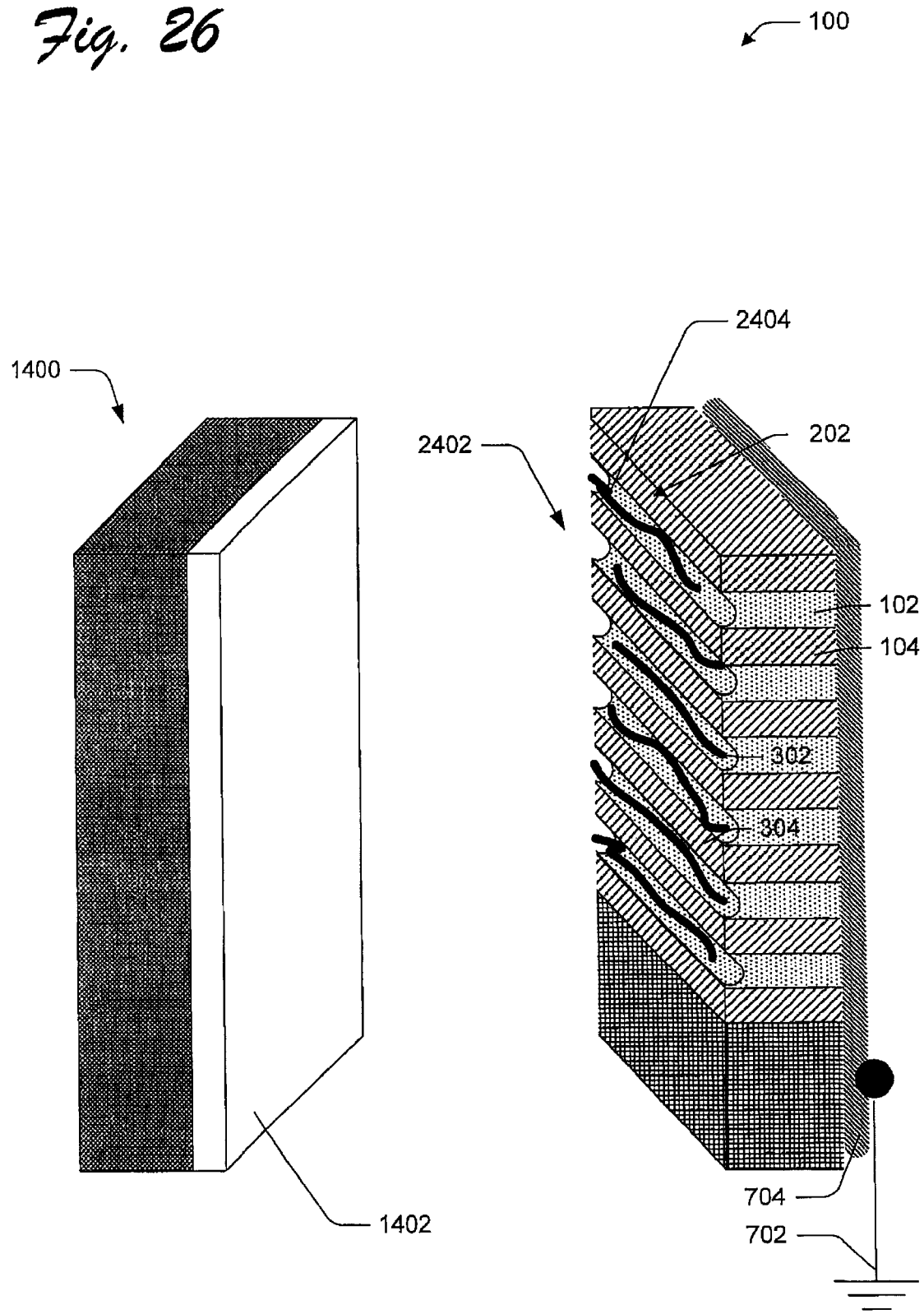
FIG. 26 illustrates a three-dimensional view of an exemplary superlattice having an exemplary array of nano-objects and an exemplary array substrate.

FIG. 26 sets forth examples of the superlattice 100, the working surface 202, the array 2402, and the array substrate 1400 (also shown in FIG. 14).

In one implementation, the array substrate 1400 includes an example of the high-adhesion layer 1402. This example of the high-adhesion layer 1402 facilitates transfer of the nano-objects 2404 of the array 2402 from the superlattice 100 to the array substrate 1400. The high-adhesion layer 1402 acts with an adhesion force greater than the adhesion force between the nano-objects 2404 and the troughs 2102.

At block 2014, the platform 500 places the corrugated surface (here the working surface 202 with the troughs 2102 and the ridges 2104) near on in contact with the array substrate 1400.

FIG. 26 shows the array substrate 1400 and the superlattice 100 prior to being placed near or in physical contact.

In one implementation, the platform 500 touches the array 2402 to the array substrate 1400. The array substrate 1400 can include the high-adhesion layer 1402 or otherwise.

In another implementation, the platform 500 places the array substrate 1400 near to the troughs 2102 but not in contact with the troughs 2102. In this implementation, the platform 500 transfers the array 2402 from the troughs 2102 to the array substrate 1400 by creating a voltage difference between the array 2402 and the array substrate 1400. This can be performed by creating a voltage difference between the sink 702 and the array substrate 1400 (such as through an electrical power source in communication with the array substrate 1400, not shown).

In still another implementation, the platform 500 places the array substrate 1400 near to the troughs 2102. In this implementation, the platform 500 transfers the array 2402 (or parts of the array 2402) from the troughs 2102 to the array substrate 1400 using corona discharge. Corona discharge is known in the art of laser printing for transferring toner particles onto paper.

In this implementation (using corona discharge), a dielectric surface carrying a uniform electric charge (charged by a corona discharge) is placed some distance from the working surface 202. An insulating substrate (such as an insulating example of the array substrate 1400) is between the working surface 202 and the dielectric surface. When the dielectric surface and the working surface 202 are sufficiently close to each other (though separated by the array substrate 1400), electrostatic pull on the array 2402 caused by the charge on the dielectric surface pulls the array 2402 to the substrate 1400. The dielectric surface can be made smaller than the working surface 202 and the array 2402. In this case parts of the array 2402 can be pulled to the substrate 1400. This allows for creation of arrays of nano-objects smaller than and/or with various physical shapes not present in the array 2402.

In each of these implementations of block 2014, the platform 500 transfers the array 2402 (or parts thereof) to the array substrate 1400.

At block 2016 the platform 500 removes the corrugated surface to leave the array 2402 of the nano-objects 2404 on the array substrate 1400. In the ongoing example, the platform 500 removes (or moves away) the working surface 202 from the array substrate 1400, thereby leaving the array 2402 on the array substrate 1400.

Figure 27:
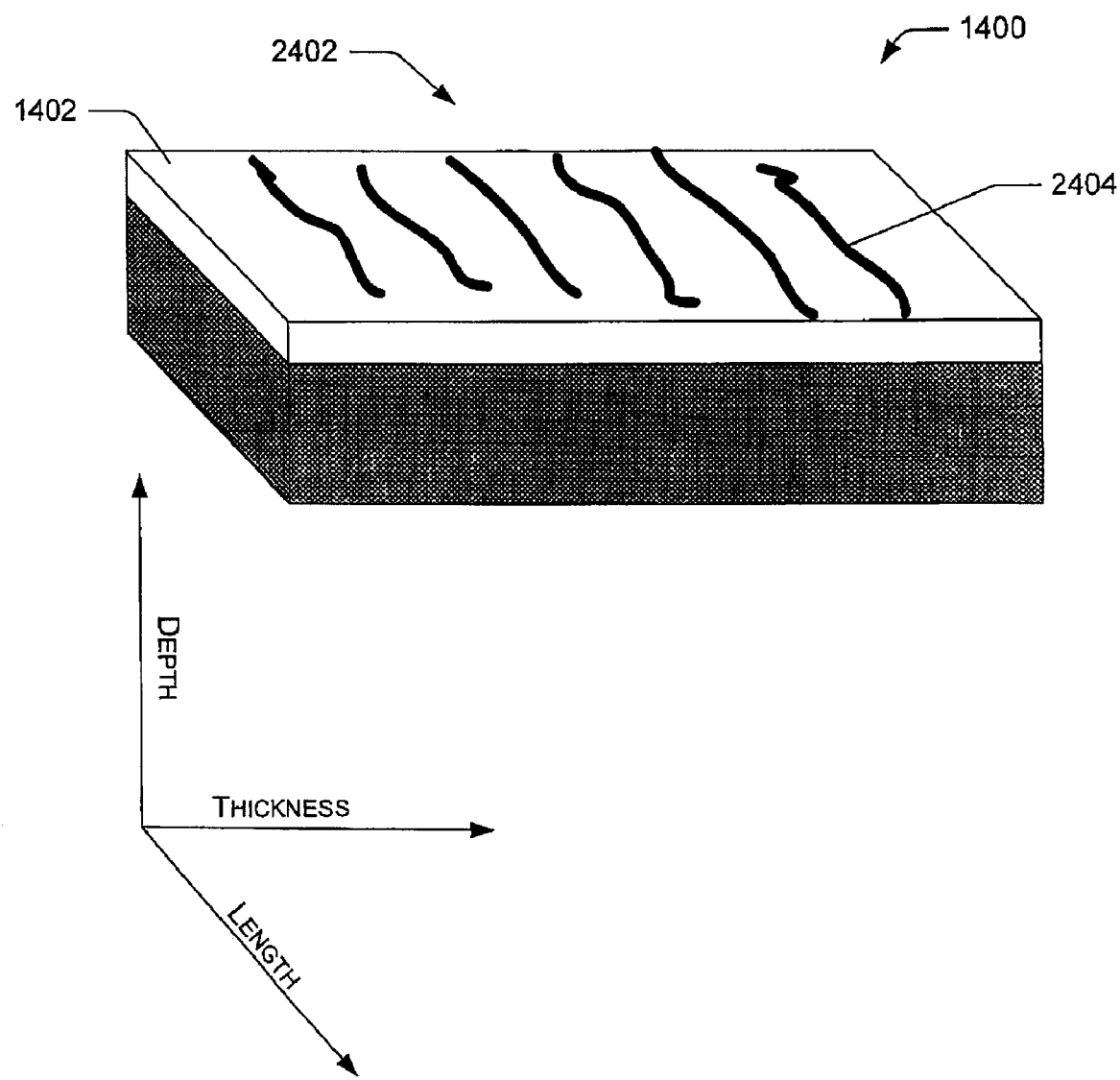
FIG. 27 illustrates a three-dimensional view of an exemplary array substrate with an exemplary array of nano-objects on one of the array substrate's surfaces and thickness, depth, and length dimensions.

FIG. 27 sets forth an example of the array substrate 1400 and the array 2402 after the nano-objects 2404 are transferred.

The platform 500 can repeat the above blocks 2012, 2014, and 2016 to create a new array that includes the array 2402 and another array. The platform 500 can apply, for instance, a second array of nano-objects or nano-wires to the array 2402 on the array substrate 1400.

This second array can be created using the processes 600, 1600, 2000, or otherwise.

The platform 500 can apply the second array to the array 2402 in various ways to create the new array. The platform 500 can, for instance, apply the second array next to the array 2402, thereby creating a new array that is twice as wide or long as the array 2402. By applying additional arrays, a larger array that is a mosaic of these additional arrays can be created.

In another implementation, the platform 500 can apply the second array to the array 2402 substantially perpendicular to the array 2402. By so doing, the platform 500 can create a cross-hatch of the array 2402 and the second array.

Figure 28:
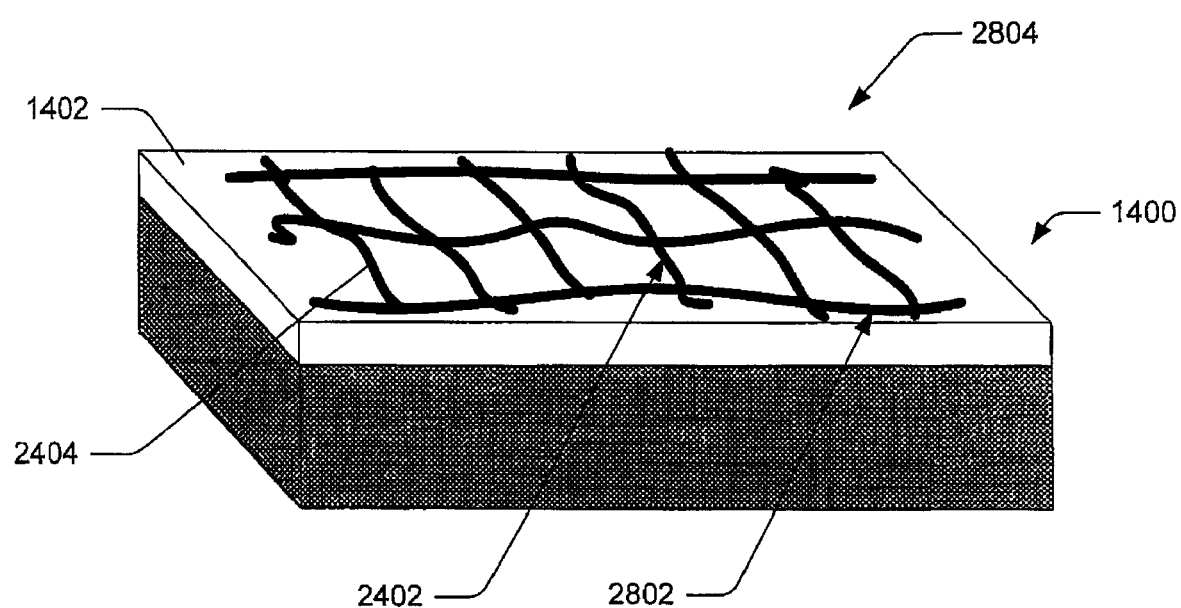
FIG. 28 illustrates a three-dimensional view of an exemplary array substrate with an exemplary cross-hatch array of nano-objects and/or nano-wires on one of the array substrate's surfaces.

FIG. 28 sets forth an example of the array substrate 1400, the array 2402, a second array 2802, and the cross-hatch array 2804. This implementation shows application of the second array 2802 on the array 2402. The array 2402 and the second array 2802 can include similar or completely different materials. For instance, the second array 2802 can be an array of nano-wires made of nickel, while the array 2402 can be an array of carbon polymer nano-tube complexes. This flexibility in creation of the resultant array (whether the shown cross-hatch array 2804 or another array) allows for many varied and useful arrays.

Thus, using the process 2000, the platform 500 can create arrays of nano-objects. The resultant array (here the array 2402), can include substantially parallel rows of the nano-objects 2404. Based on the many different types of materials and particles that can be included in the nano-objects 2404, the array 2402 can be made of rows of polymer nano-tubes, metal wires, semi-conductors, and other materials. In the case of nano-tubes, the array 2402, or an array including the array 2402 and the second array 2802, can have a length that is nanometer to centimeter in scale and a thickness and depth that is nanometer to meso-meter in scale.

Although the invention is described in language specific to structural features and methodological steps, it is to be understood that the invention defined in the appended claims is not necessarily limited to the specific features or steps described. Rather, the specific features and steps disclosed represent preferred forms of implementing the claimed invention.

What is claimed is:

1. A method for fabricating an array of nano-objects comprising:
providing a superlattice having a working surface and alternating layers of a conductive material and one or more other materials, the working surface comprising exposed edges of the alternating layers, the exposed edges of the conductive material layers being offset to form troughs relative to the exposed edges of one or more of the one or more other material layers and having a length and a thickness, the length being significantly larger than the thickness and the thickness being between 0.7 and one hundred nanometers;
charging nano-objects in a liquid bath, the charged nano-objects having a length and a thickness, the length being significantly larger than the thickness, the thickness of the charged nano-objects being less than the thickness of the exposed edges of the conductive material layers;
placing the working surface in the bath;
charging the offset, exposed edges of the conductive material layers to create a voltage difference between the offset, exposed edges of the conductive material layers and the charged nano-objects; and
collecting the charged nano-objects in the troughs to create an array of the nano-objects.

2. The method of claim 1, wherein the bath has a temperature of fifteen to thirty degrees Celsius.

3. The method of claim 1, wherein the liquid flows over the working surface.

4. The method of claim 1, wherein the liquid laminarly flows over the working surface.

5. The method of claim 1, wherein the pH of the bath is between four and nine.

6. The method of claim 1, wherein the voltage difference is between one and ten volts.

7. The method of claim 1, wherein the lengths of each of many of the collected, charged nano-objects is substantially oriented along the length of the offset, exposed edges of the conductive material layers.

8. The method of claim 1, wherein the collecting further includes:
laminarly flowing the charged nano-objects along the length of the offset, exposed edges of the conductive material layers.

9. The method of claim 1, wherein the collecting further includes:
laminarly flowing the charged nano-objects along the length of the troughs but leaving some of the nano-objects uncollected; and
introducing turbulent flow outside of the troughs to remove the uncollected nano-objects.

10. The method of claim 1, wherein the collecting further includes:
laminarly flowing the charged nano-objects along the length of the troughs but leaving some of the nano-objects uncollected; and
introducing gas bubbles into the laminar flow to create turbulence in the flow outside of the troughs to remove the uncollected nano-objects.

11. The method of claim 1, wherein the collecting further includes:
settling the charged nano-objects into the troughs by agitating the charged nano-objects.

12. The method of claim 1, wherein the collecting further includes applying a small alternating current to oscillate the charged nano-objects to aid in collecting the charged nano-objects within the troughs.

13. The method of claim 1, wherein the charging the nano-objects in the bath includes charging ions in the bath to spatially distribute some of the ions near the offset, exposed edges of the conductive material layers, wherein the spatial distribution restricts a spatial region within which an electric field is non-zero near the troughs.

14. The method of claim 1, further comprising:
removing substantially all of the nano-objects that are not collected with the troughs.

15. The method of claim 1, wherein the charged nano-objects include polymer nano-tubes complexes.

16. The method of claim 1, wherein the charged nano-objects include ionized inorganic molecules, ionized organic molecules, ionized biological molecules, ionized polymers, charged metal particles, semiconductor particles, insulating nanoparticles, metal nanowires, metal nano-needles, semiconductor nanowires, or semiconductor nano-needles.

17. The method of claim 1, further comprising:
contacting the array and the working surface to a substrate; and
separating the working surface from the substrate to release the array from the working surface.

18. The method of claim 1, further comprising:
contacting the array and the working surface to a high-adhesion layer of a substrate; and
separating the working surface from the substrate to release the array from the working surface.

19. The method of claim 1, further comprising:
providing a substrate having a second array of nano-objects;
contacting the array and the working surface to the substrate substantially perpendicular to the second array; and
separating the working surface from the substrate to release the array from the working surface to create a cross-hatch of the array and the second array.

20. The method of claim 1, further comprising:
providing a substrate having a second array of nano-objects;
contacting the array and the working surface to the substrate parallel to the second array; and
separating the working surface from the substrate to release the array from the working surface.

21. The method of claim 1, further comprising:
placing a substrate near to the working surface of the superlattice; and
transferring the array of the nano-objects from the working surface to the substrate by creating a voltage difference between the array of the nano-objects and the substrate.

22. The method of claim 1, further comprising:
placing a substrate near to the working surface of the superlattice;
charging a dielectric plate with a corona discharge; and
placing the charged, dielectric plate near the substrate to transfers a part of the array of the nano-objects from the working surface to the substrate.

23. A method for fabricating an array of nano-objects comprising:
charging nano-objects;
charging, relative to the charged nano-objects, troughs of a corrugated surface of a superlattice, the corrugated surface having ridges being substantially uncharged relative to the nano-objects;
exposing the surface to the charged nano-objects to create, within the troughs, an array of the charged nano-objects, wherein the charged nano-objects are ions within a bath and the exposing includes placing the surface within the bath.

24. The method of claim 23, wherein the troughs have a thickness between 0.7 and one hundred nanometers.

25. The method of claim 23, wherein the exposing the surface includes flowing the charged nano-objects over the troughs.

26. The method of claim 23, wherein the exposing the surface includes laminarly flowing the charged nano-objects along the troughs, and further comprising:
introducing turbulent flow outside of the troughs to remove the charged nano-objects that are not within the troughs.

27. The method of claim 23, further comprising;
settling some of the charged nano-objects that are not within the troughs into the troughs by agitating the charged nano-objects.

28. An apparatus comprising:
means for charging nano-objects;
means for charging, relative to the charged nano-objects, troughs of a corrugated surface, the corrugated surface having ridges being substantially uncharged relative to the nano-objects;
means for exposing the surface to the charged nano-objects to collect, within the troughs, a first array of the charged nano-objects, wherein the means for exposing is a flow of the charged nano-objects along the troughs.

29. The apparatus of claim 28, wherein the means for exposing is a flow of the charged nano-objects along the troughs and further comprising:
means to introduce turbulent flow outside of the troughs to remove substantially all of the charged nano-objects that are not collected within the troughs.

30. The apparatus of claim 28, further comprising:
means for settling the charged nano-objects that are partially collected within the troughs to substantially within the troughs by agitating the partially collected, charged nano-objects.

31. The apparatus of claim 28, further comprising:
means for contacting the first array and the corrugated surface to a substrate; and
means for separating the corrugated surface from the substrate to release the first array from the corrugated surface.

32. The apparatus of claim 28, further comprising:
means for providing a substrate having a second array of nano-objects;
means for contacting the first array and the corrugated surface to the substrate substantially perpendicular to the second array; and
means for separating the corrugated surface from the substrate to release the first array from the corrugated surface to create a cross-hatch of the first array and the second array.

33. The apparatus of claim 28, further comprising:
means for providing a substrate having a second array of nano-objects;
means for contacting the first array and the corrugated surface to the substrate parallel to the second array; and
means for separating the corrugated surface from the substrate to release the first array from the corrugated surface.

34. The apparatus of claim 28, further comprising:
means for placing a substrate near the troughs of the corrugated surface; and
means for transferring the first array from the troughs to the substrate by creating a voltage difference between the first array and the substrate.

* * * * *